US007838013B2

(12) United States Patent
Andersen et al.

(10) Patent No.: US 7,838,013 B2
(45) Date of Patent: Nov. 23, 2010

(54) SPECIFIC EPITOPE BASED IMMUNOLOGICAL DIAGNOSIS OF TUBERCULOSIS

(75) Inventors: Peter Andersen, Brønshøj (DK); Inger Brock, Dragør (DK); Karin Weldingh, Vaerløse (DK)

(73) Assignee: Statens Serum Institut, Copenhagen S (DK)

( * ) Notice: Subject to any disclaimer, the term of this patent is extended or adjusted under 35 U.S.C. 154(b) by 150 days.

(21) Appl. No.: 11/268,959

(22) Filed: Nov. 8, 2005

(65) Prior Publication Data

US 2006/0115847 A1 Jun. 1, 2006

Related U.S. Application Data

(63) Continuation-in-part of application No. PCT/DK2004/000314, filed on May 6, 2004.

(30) Foreign Application Priority Data

May 8, 2003 (DK) .............................. 2003 00699

(51) Int. Cl.
  A61K 39/04 (2006.01)
  A61K 39/00 (2006.01)
  C12Q 1/00 (2006.01)
(52) U.S. Cl. ................... 424/248.1; 424/9.1; 424/9.2; 424/185.1; 424/190.1; 424/243.1; 435/4; 435/7.1; 435/7.2
(58) Field of Classification Search ................. 424/9.1, 424/9.2, 185.1, 190.1, 243.1, 248.1; 435/4, 435/7.1, 7.2
See application file for complete search history.

(56) References Cited

FOREIGN PATENT DOCUMENTS

| WO | WO 95/01441 | | 1/1995 |
|----|----|----|----|
| WO | 98/44119 | | 10/1998 |
| WO | 01/04151 | A2 | 1/2001 |
| WO | WO01/04151 | * | 1/2001 |
| WO | 01/79274 | A2 | 10/2001 |
| WO | 03/093307 | A2 | 11/2003 |

OTHER PUBLICATIONS

Brock, et al.; "Specific T-Cell Epitopes for Immunoassay-Based Diagnosis of *Mycobacterium tuberculosis* Infection"; Journal of Clinical Microbiology (2004); vol. 42(6); pp. 2379-2387.
Cockle, et al.; "Identification of Novel *Mycobacterium tuberculosis* Antigens with Potential as Diagnosis Reagents or Subunit Vaccine Candidates by Comparative Genomics"; Infection and Immunity (Dec. 2002); vol. 70(12); pp. 6996-7003.
Pinxteren, et al.; "Control of latent *Mycobacterium tuberculosis* infection is dependent on CD8 T cells"; Eur. J. Immunol (2000); vol. 30; pp. 3689-3698.
Andersen, Peter; "TB Vaccines: Progress and Problems"; Trends in Immunology(Mar. 2001); vol. 22(3); pp. 160-168.

WHO 2000 Tuberculosis, Fact Sheet No. 104, WHO Homepage, www.who.org.
P. Andersen, et al., Specific Immune-Based Diagnosis of Tuberculosis, The Lancet (2000) vol. 356, p. 1099-1104.
Sandra Arend, et al., Tuberculin Skin Testing Compared With T-Cell Responses To *Mycobacterium tuberculosis*-Specific And Nonspecific Antigens For Detection Of Latent Infection In Persons With Recent Tuberculosis Contact,, Clinical and Diagnostic Laboratory Immunology (2001) vol. 8, No. 6, p. 1089-1096.
S. M. Arend, et al., Uncommon Presentations Of Tuberculosis: The Potential Value Of A Novel Diagnostic Assay Based On The *Mycobacterium tuberculosis*-Specific Antigens ESAT-6 and CFP-10, Int. J. Tuberc Lung Dis. (2001) vol. 5, No. 7, p. 680-686.
Sandra M. Arend, et al., Detection Of Active Tuberculosis Infection By T Cell Responses To Early-Secreted Antigen Target 6-kDa Protein And Culture Filtrate Protein 10, The Journal of Infectious Diseases (2000) vol. 181, p. 1850-1854.
M. A. Behr, et al., Comparative Genomics Of BCG Vaccines By Whole-Genome DNA Microarray, Science (1999) vol. 284, p. 1520-1523.
I. Brock, et al., Performance Of Whole Blood IFN-γ Test for Tuberculosis Diagnosis Based On PPD Or The Specific Antigens ESAT-6 And CFP-10, Int. J. Tuberc. Lung Dis. (2001) vol. 5, No. 5, p. 462-467.
Ajit Lalvani, et al., Enhances Contact Tracing And Spatial Tracking Of *Mycobacterium tuberculosis* Infection By Enumeration Of Antigen-Specific T Cells, The Lances (2001) vol. 357, p. 2017-2021.
Ajit Lalvani, et al., Rapid Detection Of *Mycobacterium tuberculosis* Infection By Enumeration Of Antigen-Specific T Cells, Am J. Respir. Cirt. Care Med. (2001) vol. 163, p. 824-828.
A. David Lein, et al., Cellular Immune Responses To ESAT-6 Discriminate Between Patients With Pulmonary Disease Due To Mycobacterium Avium Complex and Those With Pulmonary Disease Due To *Mycobacterium tuberculosis*, Clinical And Diagnostic Laboratory Immunology (1999) vol. 6, No. 4, p. 606-609.

(Continued)

*Primary Examiner*—Rodney P. Swartz
(74) *Attorney, Agent, or Firm*—Frommer Lawrence & Haug LLP; Sandra Kuzmich; Russell A. Garman

(57) ABSTRACT

The currently used method for immunological diagnosis of tuberculosis infection, the tuberculin skin test, is problematic for a number of reasons; it has low specificity in BCG vaccinated individuals, a high interobserver variance and requires skill to be read and interpreted. Furthermore it requires an extra visit to the clinic to have the test read. Both people vaccinated with BCG and those exposed to non-tuberculosis mycobacteria give a positive skin test result similar to that seen in a TB infected individual. This also applies for purified protein derivative (PPD) when used in a blood cell based test. The present invention discloses the development of an immunological TB diagnostic tool based on a combination of epitopes from proteins encoded by regions of the M. tuberculosis (M. tub.) genome, that are not present in the BCG vaccine strain or in the most common non-tuberculosis mycobacteria.

4 Claims, 5 Drawing Sheets

OTHER PUBLICATIONS

Figure 1:
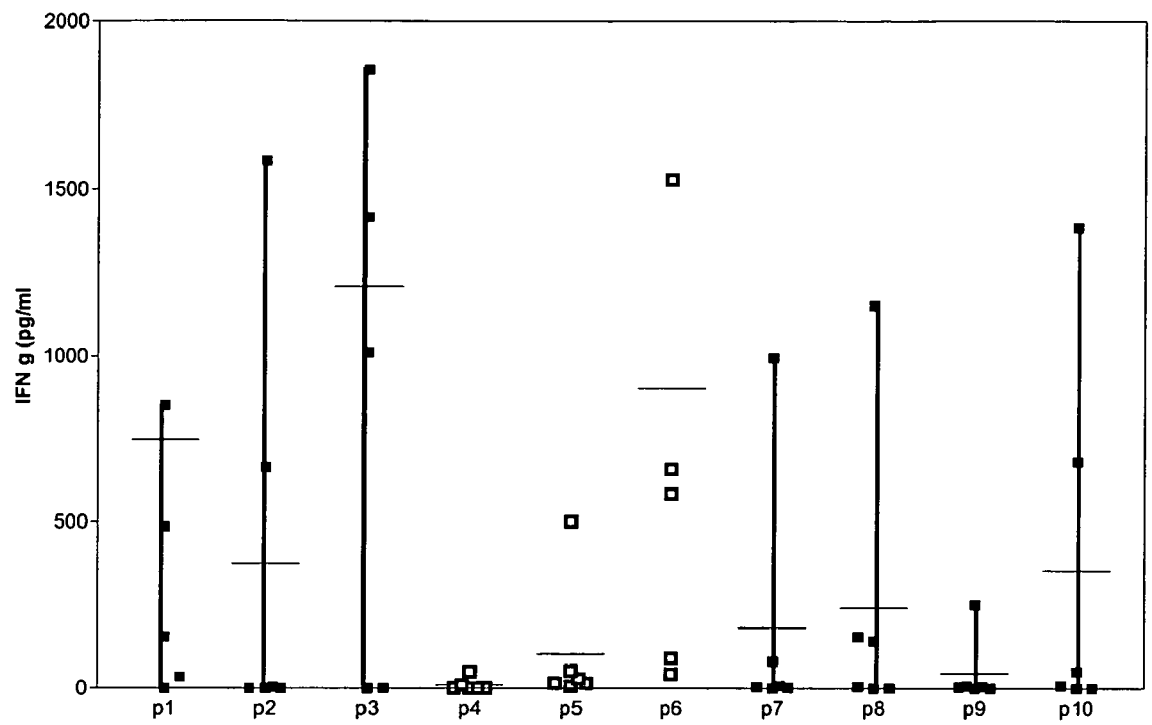
Figure 1:
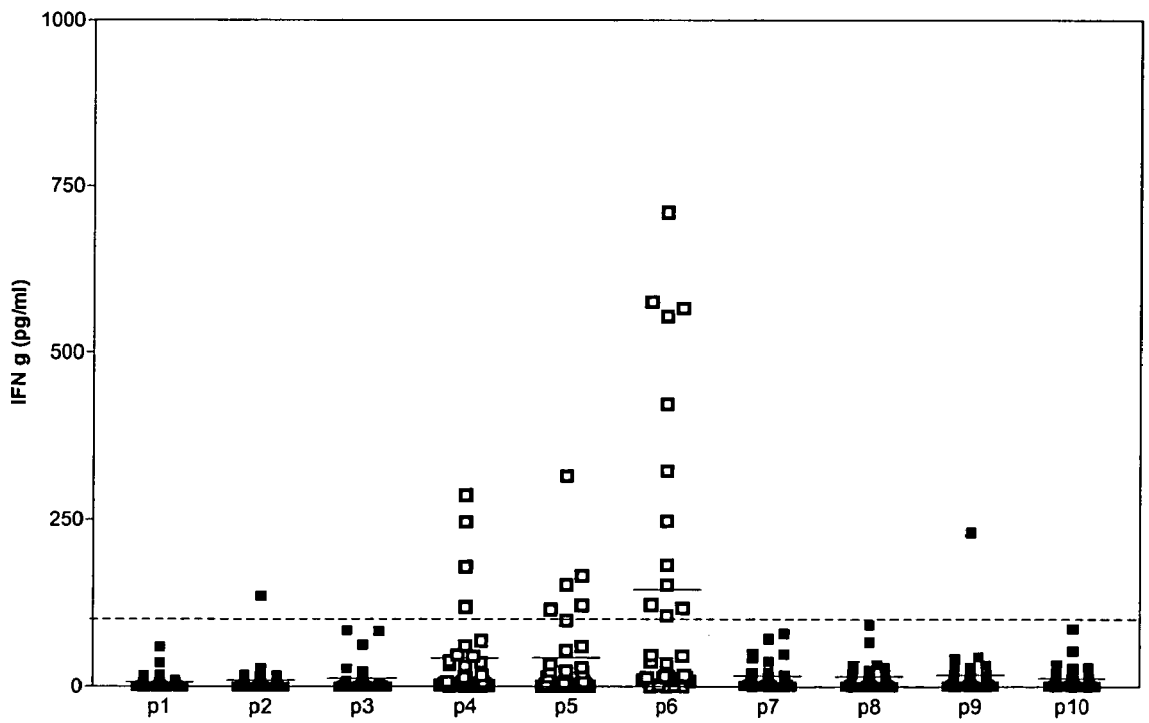

Martin E. Munk, et al., Use of ESAT-6 and CFP-10 Antigens for Diagnosis of Extrapulmonary Tuberculosis, The Journal of Infectious Diseases (2001) vol. 183, p. 175-176.

Pernille Ravn, et al., Human T Cell Responses To The ESAT-6 Antigen From *Mycobacterium tuberculosis*, The Journal of Infections Diseases (1999) vol. 179, p. 637-645.

Timo Ulrichs, et al., Increased Numbers Of ESAT-6- And Purified Protein Derivative-Specific Gamma Interferon-Producing Cells In Subclinical And Active Tuberculosis Infection, Infection And Immunity (2000) vol. 68, No. 10, p. 6073-6076.

A. H. Laurens van Pinxteren, et al., Diagnosis Of Tuberculosis Based On The Two Specific Antigens ESAT-6 And CFP10, Clinical And Diagnostic Laboratory Immunology (2000) vol. 7, No. 2, p. 155-160.

H. M. Vordermeier, et al., Use Of Synthetic Peptides Derived From The Antigens ESAT-6 And CFP-10 For Differential Diagnosis Of Bovine Tuberculosis In Cattle, Clinical And Diagnostic Laboratory Immunology (2001) vol. 8, No. 3, p. 571-578.

Mark H. Zweig, et al., Receiver-Operating Characteristic (ROC) Plots: A Fundamental Evaluation Tool In Clinical Medicine, Clinical Chemistry (1993) vol. 39, No. 4, p. 561-577.

* cited by examiner

Epitope mapping Rv3878 peptides. 7 T cell lines

SPECIFIC EPITOPE BASED IMMUNOLOGICAL DIAGNOSIS OF TUBERCULOSIS

REFERENCE TO RELATED APPLICATIONS

The present invention is a continuation-in-part of International Patent Application PCT/DK2004/000314 filed May 6, 2004 and published as WO 2004/099771 on Nov. 18, 2004, which claims priority from Denmark Patent Application PA 2003 00699 filed May 8, 2003. Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

FIELD OF INVENTION

The present invention discloses compositions for use as a pharmaceutical or diagnostic reagent and a diagnostic tool for cell mediated immunological diagnosis of tuberculosis.

GENERAL BACKGROUND

Tuberculosis (TB) is a major cause of morbidity and mortality throughout the world. It is estimated that nearly 1% of the worlds population is newly infected each year and that approximately ⅓ of the worlds population is latently infected with *Mycobacterium Tuberculosis* tuberculosis (*M. tuberculosis*) the microorganism that causes the disease in man.

Immunocompetent individuals infected with *M. tuberculosis* in general have a lifetime risk of 10% for developing active TB, this risk increases many times if the individual is co infected with HIV. If left untreated each person with active pulmonary TB will infect 10 to 15 people each year [WHO, 2000]. For these reasons it is important to be able to detect TB infected individuals at an early stage of infection, to prevent the progression to active contagious TB (prophylactic treatment) or to treat the TB disease at an early stage. Therefore a fast and accurate diagnosis of *M. tuberculosis* infection is an important element of global health measures to control the disease.

Current diagnostic assays to determine *M. tuberculosis* infection include: culture, microscopy and PCR of relevant patient material, chest X-rays and the standard tuberculin skin test (TST). The three first methods are based on the identification of the *M. tuberculosis* bacteria and therefore depend on presence of bacteria in the sample. This demands a certain bacterial load and access to the infection site, and is therefore not suitable in early diagnosis. Chest X-ray is insensitive and only applicable in tuberculosis of the lung and in a progressed stage.

The standard tuberculin skin test, displaying a delayed type hypersensitivity reaction (DTH) is a simple and inexpensive assay, based on immunological recognition of mycobacterial antigens in exposed individuals. However it is far from ideal in detecting *M. tuberculosis* infection. It employs intradermal injection of purified protein derivative (PPD) which is a crude and poorly defined mixture of mycobacterial antigens some of which are shared with proteins from the vaccine sub-strain *M. bovis* bacille Calmette-Guèrin (BCG) and from non-tuberculosis environmental mycobacteria. This broad cross-reactivity of PPD causes the poor specificity of the TST, leading to a situation where BCG vaccination and exposure to non-tuberculosis mycobacteria gives a test result similar to that seen in a *M. tuberculosis* infected individual. The same concern applies for PPD when used in a blood cell based test. It is this immunological detection of *M. tuberculosis* infection our invention will improve.

*M. tuberculosis* infection mediates a strong cell mediated immune response and detection of T cells that are specific for this bacterium would be a suitable method to detect infection [Andersen, 2000].

To make a sensitive and specific cell mediated immunologically (CMI) based diagnostic reagent for *M. tuberculosis* infection two criteria needs to be meet to improve the accuracy:

The reagent should be broadly recognized by *M. tuberculosis* infected persons

The reagent should be specific for the tuberculosis bacteria, discriminating between TB infection and vaccination with the attenuated BCG strain or exposure to non pathogenic environmental mycobacteria.

A highly specific reagent candidate should therefore be sought among antigens from the RD regions (regions of deletion) of the *M. tuberculosis* genome. These regions represent genomic deletions from the *M. bovis* BCG vaccine strain compared to the virulent *M. tuberculosis* strain [Behr, 1999]. Therefore, in theory, antigens from these regions would be excellent candidates for a TB diagnostic, i.e. they should not be recognized by healthy uninfected persons independent on their BCG vaccine status or exposure to non-pathogenic mycobacterial strains.

However out of all the predicted genomic ORF's (open reading frames) deleted from BCG it is not known per se which ones are in fact expressed into proteins and furthermore the immunoreactivity remains unknown until tested with sensitised lymphocytes from *M. tuberculosis* infected individuals either in a whole blood assay or on PBMC.

In our laboratory we have screened a large proportion of the deleted ORF's and only 10-15 of them were immunoreactive.

The diagnostic potential of the CFP 10 antigen (Rv3874), and The Esat 6 antigen (Rv 3875) two low molecular proteins from the RD 1 region, in a CMI based test is already well known [Arend, 2000; Arend 2001a; Arend 2001b; Brock, 2001; Lalvani, 2001a; Lalvani, 2001b; Lein, 1999; Munk, 2001; Ravn, 1999; Ulrichs, 2000; van Pinxteren, 2000; Vordermeier, 2001], also Rv1980 is well known as a CMI diagnostic antigen and in skin-test based tests. CFP 10 and Esat 6 proteins are very specific but each one used alone gives a sensitivity of about 75% which on its own is too low for a reliable diagnostic. Therefore combinations with other *M. tuberculosis* specific antigens needs to be found to broaden the recognition and thereby give a higher sensitivity without compromising the specificity.

Consequently there is a great need for a specific diagnostic reagent, comprising a cocktail of antigens or fusion polypeptides, which can be used either in vivo or in vitro to detect *M. tuberculosis* infections in humans and animals, and discriminate between TB infection and vaccination with the attenuated BCG strain or exposure to non pathogenic environmental mycobacteria.

We hereby present a cell mediated immunological (CMI) TB diagnostic based on a combination of epitopes from regions of the *M. tuberculosis* genome that are not present in the BCG vaccine strain or in non-tuberculosis mycobacteria. This diagnostic test has the advantage of being specific for *M. tuberculosis* infection, not recognizing BCG vaccinated individuals or individuals exposed to non-pathogenic mycobacteria. Furthermore the immunological test is not dependent upon the presence of *M. tuberculosis* bacteria in the sample and the test can be applied in any clinical form of infection with a high sensitivity.

SUMMARY OF THE INVENTION

The invention is related to detecting infections caused by species of the tuberculosis complex (*M. tuberculosis, M. bovis, M. africanum*) and discriminate between TB infection and vaccination with the attenuated BCG strain or exposure to non-pathogenic environmental mycobacteria. The invention discloses specific diagnostic reagents, which can be used either in vivo or in vitro to detect a cellular response to *M. tuberculosis* infections. By using a cocktail or fusion protein of immunogenic epitopes from several different antigens we broaden the recognition, thereby making the test more sensitive.

DETAILED DISCLOSURE OF THE INVENTION

The present invention discloses a composition comprising a combination of fragments from two or more substantially pure polypeptides selected from a) amino acid sequences selected from Rv2654, Rv2653 and Rv3873 b) an amino acid sequence analogue having at least 70% sequence identity to any one of the sequences in (a) and at the same time being immunogenic.

The present invention further discloses a composition comprising a combination of fragments from two or more substantially pure polypeptides selected from a) amino acid sequences selected from Rv2654, Rv2653 and Rv3873 b) an amino acid sequence analogue having at least 70% sequence identity to any one of the sequences in (a) and at the same time being immunogenic, and additionally a fragment of Rv3878 and/or an amino acid sequence having at least 70% (such as at least 75%, at least 80%, at least 85%, at least 90% or at least 95%) sequence identity to a fragment of Rv3878

The present invention also discloses a composition comprising a combination of fragments from three or more substantially pure polypeptides selected from a) amino acid sequences selected from Rv2654, Rv2653, Rv3873 and Rv3878 b) an amino acid sequence analogue having at least 70% sequence identity to any one of the sequences in (a) and at the same time being immunogenic.

The compositions of the invention can be used as a pharmaceutical or diagnostic reagent, and comprise advantageous one or more additives such as preservatives, detergents etc. The composition can be in solid form, or it can be a liquid.

The invention also discloses a composition wherein each of the polypeptide fragments are present as separate entities or some or all are fused together optionally via linkers or spacers (such as an amino acid or an amino acid sequence).

The invention further discloses the use of this composition for the preparation of a pharmaceutical composition, e.g. for diagnosis of tuberculosis caused by virulent mycobacteria, e.g. by *Mycobacterium tuberculosis, Mycobacterium africanum* or *Mycobacterium bovis.*

Another embodiment of the invention is a diagnostic tool comprising a composition mentioned above. Still another embodiment of the invention is a CMI diagnostic tool comprising a composition mentioned above.

The invention also discloses the above mentioned compositions and diagnostic tools further comprising ESAT6 and/or CFP10 and/or Rv1980, or subsequences hereof.

The diagnostic method which is performed with above mentioned compositions and diagnostic tools is based on cellular mediated immunological (CMI) recognition of antigens released from the *M. tuberculosis* bacteria during infection. Therefore the test does not require presence of the bacteria as traditional culture, microscopy and PCR methods, this means that the test can be applicated early in the infection phase and that the test is applicable at any site of infection.

Therefore the method is ideal in contact tracing as a replacement for the currently used TST. The method holds the following improvements compared to the skin-test:

- If done in vitro it requires only one blood sample and there is therefore no need to come back to the clinic two days after application to get the test read as is the case with the skin-test.
- Because the antigens are selected from regions deleted from the BCG vaccine strain, and the antigens furthermore are tested carefully for recognition in a BCG vaccinated population and only specific regions are included, the test is specific also in a BCG vaccinated population. This is not the case for the traditional skin-test based on PPD, or other immunological tests based on PPD.

Previously only one antigen (Esat 6 or Rv1980) have been used in CMI based *M. tuberculosis* tests. The test presented here takes advantage of the broader recognition obtained from using more than one *M. tuberculosis* specific antigen. In our tests we saw that using only CFP 10 or Esat 6 the sensitivity unexpectedly rose from 60-67% respectively, to 93% using a combination of four specific regions from four different proteins.

The present invention also discloses an improved skin test and a reagent for such a skin test on an animal, including a human being, with the composition mentioned above. The skin test being: intradermally injecting in the animal or applying on the animals skin, e.g. with a patch or plaster, a composition of the present invention. A positive skin response at the location of injection or application being indicative of the animal having tuberculosis, and a negative skin response at the location of injection or application being indicative of the animal not having tuberculosis.

The invention further relates to the novel polypeptides, such as a polypeptide selected from the group consisting of a fragment of any of: Rv2654, Rv2653, Rv3873 or Rv3878; and an amino acid sequence having at least 70% (such as at least 75%, at least 80%, at least 85%, at least 90% or at least 95%) sequence identity to said fragment. A fragment is understood to be an amino acid sequence which is shorter than the native polypeptide, e.g. a truncated form of the polypeptide or a sequence consisting of e.g. 6-20 amino acids, said sequence comprising a T-cell epitope.

Also, the invention relates to a polypeptide which comprises an amino acid sequence selected from the group consisting of
a) SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50; and
b) an amino acid sequence having at least 70% (such as at least 75%, at least 80%, at least 85%, at least 90% or at least 95%) sequence identity to a fragment in a).

It should be understood that the native, full-length polypeptides Rv2654, Rv2653, Rv3873 and Rv3878 are excluded. In a presently preferred embodiment, the polypeptide comprises at least 2 (such as at least 3, at least 4, at least 5, at least 6, at least 7, at least 8, at least 9, at least 10, at least 15, at least 20) amino acid sequences independently selected from a) or b), optionally coupled via a linker or spacer (such as an amino acid or an amino acid sequence). This embodiment comprises a polypeptide which in its amino acid sequence contains several or all fragments (as defined in table 4, optionally with overlapping amino acids removed, or T-cell epitopes of said sequences) of a specific full-length polypeptide (Rv2654, Rv2653, Rv3873 or Rv3878).

It is not necessary that the polypeptides of the invention comprises the fragments SEQ ID NOs: 1-50 in their full length, as a sequence of only 6-9 amino acids (T-cell epitope) seems to be sufficient for eliciting an immune response. As it is possible for a skilled person to determine the exact and minimal amino acid sequence for the T-cell epitope embedded in SEQ ID Nos: 1-50, the present invention also relates to polypeptides comprising said T-cell epitopes (or analogues thereto) without the specific additional amino acids as defined in SEQ ID Nos: 1-50, to fusion proteins comprising said T-cell epitopes (optionally coupled via a linker or spacer), and to compositions comprising such polypeptides or fusion proteins.

Further embodiments of the invention are described in the examples and in the claims.

DEFINITIONS

Sensitivity

Numbers of true positive results of the assay divided by numbers of all positive individuals tested.

Specificity

Numbers of true negative results divided by numbers of all negative controls tested.

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991, Immunology 72(3):317-22 or with dodecanoyl chloride as described by Lustig et al. 1976, Cell Immunol 24(1): 164-72), by comprising prosthetic groups, or by containing additional amino acids such as e.g. a his-tag or a signal peptide.

Each polypeptide may thus be characterized by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". These are defined according to the following table. Amino acids in the same block in the second column and preferably in the same line in the third column may be substituted for each other. The amino acids in the third column are indicated in one-letter code.

| | | |
|---|---|---|
| ALIPHATIC | Non-polar | G, A, P |
| | | I, L, V |
| | Polar-uncharged | C, S, T, M |
| | | N, Q |
| | Polar-charged | D, E |
| | | K, R |
| AROMATIC | | H, F, W, Y |

A preferred polypeptide within the present invention is a fragment of an immunogenic antigen from *M. tuberculosis*. Such antigen can for example be derived from the *M. tuberculosis* cell and/or *M. tuberculosis* culture filtrate. Thus, a polypeptide comprising an immunogenic portion of one of the above antigens may consist entirely of the immunogenic portion, or may contain additional sequences. The additional sequences may be derived from the native *M. tuberculosis* antigen or be heterologous and such sequences may, but need not, be immunogenic.

Each polypeptide is encoded by a specific nucleic acid sequence. It will be understood that such sequences include analogues and variants hereof wherein such nucleic acid sequences have been modified by substitution, insertion, addition or deletion of one or more nucleic acid. Substitutions are preferably silent substitutions in the codon usage which will not lead to any change in the amino acid sequence, but may be introduced to enhance the expression of the protein.

In the present context the term "substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. free of any other antigen from bacteria belonging to the tuberculosis complex or a virulent mycobacterium. This can be accomplished by preparing the polypeptide fragment by means of recombinant methods in a non-mycobacterial host cell as will be described in detail below, or by synthesizing the polypeptide fragment by the well-known methods of solid or liquid phase peptide synthesis, e.g. by the method described by Merrifield (R. B. Fed. Proc. Am. Soc. Ex. Biol. 21: 412, 1962 and J. Am. Chem. Soc. 85: 2149, 1963) or variations thereof.

By the term "virulent mycobacterium" is understood a bacterium from the tuberculosis complex, capable of causing the tuberculosis disease in an animal or in a human being. Examples of virulent mycobacteria are *M. tuberculosis, M. africanum* and *M. bovis*. Examples of relevant animals are cattle, possums, badgers and kangaroos.

By "a TB patient" is understood an individual with culture or microscopically proven infection with virulent mycobacteria, and/or an individual clinically diagnosed with TB and who is responsive to anti-TB chemotherapy. Culture, microscopy and clinical diagnosis of TB are well known by any person skilled in the art.

By the term "PPD-positive individual" is understood an individual with a positive Mantoux test or an individual where PPD induces a positive in vitro recall response determined by release of IFN-γ.

By the term "delayed type hypersensitivity reaction" (DTH) is understood a T-cell mediated inflammatory response elicited after the injection of a polypeptide into, or application to, the skin, said inflammatory response appearing 72-96 hours after the polypeptide injection or application.

By the term "IFN-γ" is understood interferon-gamma. The measurement of IFN-γ is used as an indication of an immunological response.

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length e.g. from 10 to 10000 nucleotides, depending on the use. When the nucleic acid molecule is use in a method for producing a polypeptide according to the invention, a molecule encoding at least one epitope is preferably used, having a length from about 18 to about 1000 nucleotides, the molecule being optionally inserted into a vector. When the nucleic acid molecule is used as a probe, or as a primer, a molecule having a length of 10-100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives).

The term "stringent" when used in conjunction with hybridization conditions is as defined in the art, i.e. the hybridization is performed at a temperature not more than 15-20° C. under the melting point Tm, cf. Sambrook et al, 1989, Molecular Cloning; A laboratory manual, Cold Spring Harbor Laboratories, NY, pages 11.45-11.49. Preferably, the conditions are "highly stringent", i.e. 5-10° C. under the melting point Tm.

By the term "linker" is understood any molecule being able to fuse the antigens (amino acid sequences). The term encompasses molecules being able to react with both the antigens, e.g. fusing the antigens C-terminal to N-terminal, N-terminal to N-terminal or C-terminal to C-terminal. Although such terminal fusions are presently preferred, the term also encompasses linkers binding to other parts of the antigens. Examples of molecules being able to fuse the antigens N-terminal to N-terminal is a molecule with two or more groups that are able to form a bond with a amino group, e.g. a molecule with two or more carboxylic acid groups. A presently preferred molecule is a dicarboxylic acid.

Examples of molecules being able to fuse the antigens C-terminal to C-terminal is a molecule with two or more groups that are able to form a bond with a carboxylic acid group, e.g. a molecule with two or more amino groups. A presently preferred molecule is a diamine molecule.

Examples of molecules being able to fuse the antigens C-terminal to N-terminal is a molecule with at least one group that is able to form a bond with an amino group and with at least one group that is able to form a bond with a carboxylic acid group, e.g. a molecule with both an amino group and a carboxylic acid group. Examples of such a molecule is an amino acid, e.g. an α-amino acid, a peptide and a polypeptide, such a peptide or polypeptide having e.g. from 2 to 1000 amino acid units. A presently preferred molecule is a peptide having a sequence of 1 to 20 amino acids, such as 2-10 amino acids.

Also, a linker or spacer can be introduced between the antigens being fused in order to enhance the immunogenicity of the fusion molecule. The linker could e.g. 1) introduce one or more protease cleavage sites which would lead to a cleavage of the fusion molecule in the macrophage, 2) introduce a sequence leading to polymerization of the fusion molecule, 3) incorporate a sequence facilitating transport of the fusion molecule across the cell membrane leading to MHC I presentation, or 4) induce a different folding of the protein leading to an altered folding of the fusion molecule and thereby a different processing resulting in presentation of another group of epitopes. The term "linker" includes such linkers.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

Sequence Identity

The term "sequence identity" indicates a quantitative measure of the degree of homology between two amino acid sequences of equal length or between two nucleotide sequences of equal length. The two sequences to be compared must be aligned to best possible fit possible with the insertion of gaps or alternatively, truncation at the ends of the protein sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (Pearson W. R and D. J. Lipman (1988) PNAS USA 85:2444-2448) (see the National Center for Biotechnology Information website, maintained by the National Institutes of Health). In one aspect of the invention, alignment is performed with the sequence alignment method ClustalW with default parameters as described by Thompson J., et al 1994 Nucleic Acids Res 22:4673-4680, available at the European Bioinformatics Institute website.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%.

Immunogenic Epitope

An immunogenic epitope of a polypeptide is a part of the polypeptide, which elicits an immune response in an animal or a human being, and/or in a biological sample determined by any of the biological assays described herein. The immunogenic epitope of a polypeptide may be a T-cell epitope or a B-cell epitope. Immunogenic epitope can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn et al 1999).

In order to identify relevant T-cell epitopes which are recognized during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-γ assay described herein. Another method utilizes overlapping oligopeptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For the detection of MHC class I epitopes it is possible to predict peptides that will bind (Stryhn et al. 1996 Eur. J. Immunol. 26:1911-1918) and hereafter produce these peptides synthetic and test them in relevant biological assays e.g. the IFN-γ assay as described herein. The peptides preferably having a length of e.g. 8 to 11 amino acid residues derived from the polypeptide. B-cell epitopes can be determined by analysing the B cell recognition to overlapping peptides covering the polypeptide of interest as e.g. described in Harboe et al 1998, Infect. Immun. 66:2; 717-723.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 20 amino acid residues will prove to be most efficient as MHC class II epitopes and therefore especially preferred lengths of the polypeptide fragment used in the inventive method are 18, such as 15, 14, 13, 12 and even 11 amino acid residues. It is expected that the peptides having a length of between 7 and 12 amino acid residues will prove to be most efficient as MHC class I epitopes and therefore especially preferred lengths of the polypeptide fragment used in the inventive method are 11, such as 10, 9, 8 and even 7 amino acid residues.

Immunogenic portions (fragments) of polypeptides, comprising the immunogenic epitope, may be recognized by a broad part (high frequency) or by a minor part (low frequency) of the genetically heterogenic human population. In addition some immunogenic portions induce high immunological responses (dominant), whereas others induce lower, but still significant, responses (subdominant). High frequency><low frequency can be related to the immunogenic portion binding to widely distributed MHC molecules (HLA type) or even by multiple MHC molecules (Kilgus et al. J Immunol. 1991 Jan. 1; 146(1):307-15, Sinigaglia et al Nature 1988 Dec. 22-29; 336(6201):778-80).

Variants

A common feature of the polypeptides of the compositions of the invention is their capability to induce an immunological response as illustrated in the examples. It is understood that a variant of a polypeptide of the invention produced by substitution, insertion, addition or deletion is also immunogenic determined by any of the assays described herein.

Immune Individual

An immune individual is defined as a person or an animal, which has cleared or controlled an infection with virulent mycobacteria or has received a vaccination with *M. bovis* BCG.

Immunogenic

An immunogenic polypeptide is defined as a polypeptide that induces an immune response in a biological sample or an individual currently or previously infected with a virulent mycobacterium.

CMI Diagnosis

The immune response may be monitored by one of the following methods:

An in vitro cell mediated immune (CMI) response is determined by release of a relevant cytokine such as IFN-γ, from lymphocytes withdrawn from an animal or human being currently or previously infected with virulent mycobacteria, or by detection of proliferation of these T cells. The induction being performed by the addition of the polypeptide or the immunogenic portion to a suspension comprising preferably from $1 \times 10^5$ cells to $1 \times 10^6$ cells per well. The cells being isolated from either the blood, the spleen, the liver or the lung and the addition of the polypeptide or the immunogenic portion resulting in a concentration of for example 1-200 μg per ml suspension and the stimulation being performed from two to five days. For monitoring cell proliferation the cells are pulsed with radioactive labeled Thymidine and after 16-22 hours of incubation detecting the proliferation by liquid scintillation counting. A positive response being a response more than background plus two standard deviations. The release of IFN-γ can be determined by the ELISA method, which is well known to a person skilled in the art. A positive response being a response more than background plus two standard deviations. Other cytokines than IFN-γ could be relevant when monitoring the immunological response to the polypeptide, such as IL-12, TNF-α, IL-4, IL-5, IL-10, IL-6, TGF-β. Another and more sensitive method for determining the presence of a cytokine (e.g. IFN-γ) is the ELISPOT method where the cells isolated from either the blood, the spleen, the liver or the lung are diluted to a concentration of preferable of 1 to $4 \times 10^6$ cells/ml and incubated for 18-22 hrs in the presence of the polypeptide or the immunogenic portion resulting in a concentration of preferably 1-200 μg per ml. The cell suspensions are hereafter diluted to 1 to $2\times10^6$/ml and transferred to Maxisorp plates coated with anti-IFN-γ and incubated for preferably 4 to 16 hours. The IFN-γ producing cells are determined by the use of labelled secondary anti-IFN-γ antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

A simpler and yet sensitive method is the use of whole blood samples without prior isolation of mononuclear cells. With this method a sample of heparinized whole blood (with or without prior lysis of the erythrocytes) in an amount of 50-1000 ml and incubation being performed in 18 hours to 6 days with the polypeptide or composition of the invention resulting in a concentration of preferably 1-200 μg/ml suspension. The supernatant are harvested and the release of IFN-γ (or any other relevant released cytokine) can be determined by the ELISA method, which is well known to a person skilled in the art.

The invention therefore also relates to an in vitro method for diagnosing ongoing or previous sensitisation in an animal or a human being with a virulent mycobacterium, the method comprising providing a blood sample from the animal or human being, and contacting the sample from the animal with the polypeptide or the composition of the invention, a significant release into the extracellular phase of at least one cytokine by mononuclear cells in the blood sample being indicative of the animal being sensitised. A positive response being a response more than release from a blood sample derived from a patient without the TB diagnosis plus two standard deviations.

An in vitro CMI response may also be determined by the use of T cell lines derived from an immune individual or an *M. tuberculosis* infected person where the T cell lines have been driven with either live mycobacteria, extracts from the bacterial cell or culture filtrate for 10 to 20 days with the addition of IL-2. The induction being performed by addition of preferably 1-200 μg polypeptide per ml suspension to the T cell lines containing for example $1\times10^5$ cells to $3\times10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo CMI response (e.g. skin-test, transdermal skin-test, patch skin test) which may be determined as a positive DTH response after intradermal injection or local application patch of at preferably 1-200 μg of each polypeptide in the composition of the invention to an individual who is clinically or subclinically infected with a virulent *Mycobacterium*, a positive response having a diameter of at least 5 mm 72-96 hours after the injection or application.

Preparation Methods

In general, *M. tuberculosis* antigens, and DNA sequences encoding such antigens, may be prepared using any one of a variety of procedures.

They may be purified as native proteins from the *M. tuberculosis* cell or culture filtrate by procedures such as those described above. Immunogenic antigens may also be produced recombinantly using a DNA sequence encoding the antigen, which has been inserted into an expression vector and expressed in an appropriate host. Examples of host cells are *E. coli*. The polypeptides or immunogenic portion hereof can also be produced synthetically having fewer than about 100 amino acids, and generally fewer than 50 amino acids and may be generated using techniques well known to those ordinarily skilled in the art, such as commercially available solid-phase techniques where amino acids are sequentially added to a growing amino acid chain.

In the construction and preparation of plasmid DNA encoding the polypeptide, a host strain such as *E. coli* can be used. Plasmid DNA can then be prepared from overnight cultures of the host strain carrying the plasmid of interest, and purified using e.g. the Qiagen Giga-Plasmid column kit (Qiagen, Santa Clarita, Calif., USA) including an endotoxin removal step.

Fusion Proteins

Besides being separate entities two or more of the immunogenic polypeptides may also be produced as fusion proteins, by which methods superior characteristics of the polypeptide of the invention can be achieved. For instance, fusion partners that facilitate export of the polypeptide when produced recombinantly, fusion partners that facilitate purification of the polypeptide, and fusion partners which enhance the immunogenicity of the polypeptide fragment of the invention are all interesting possibilities. Therefore, the invention also pertains to a fusion polypeptide comprising at least two (such as 2, 3, 4, 5, 6, 7, 8, 9, 10 or more) polypeptide or immunogenic fragment defined above and optionally at least one additional fusion partner, and to compositions comprising fusion proteins. The fusion partner can, in order to enhance immunogenicity, be another polypeptide derived from *M. tuberculosis*, such as of a polypeptide fragment derived from a bacterium belonging to the tuberculosis complex, such as ESAT-6, TB10.4, CFP10, RD1-ORF2, Rv1036, MPB64, MPT64, Ag85A, Ag85B (MPT59), MPB59, Ag85C, 19 kDa lipoprotein, MPT32 and alpha-crystallin, or at least one T-cell epitope of any of the above mentioned antigens (Skjøt et al 2000, Infect. Immun 68:1; 214-220; WO0179274; WO0104151; Rosenkrands et al 1998, Infect. Immun 66:6; 2728-2735; Nagai et al 1991, Infect. Immun 59:1; 372-382). The invention also pertains to a fusion polypeptide comprising mutual fusions of two or more (such as 3, 4, 5, 6, 7, 8, 9, 10 or more) of the polypeptides (or immunogenic portions thereof) of the invention.

In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; gluthatione S-transferase; β-galactosidase; or poly-histidine. Fusion proteins can be produced recombinantly in a host cell, which could be *E. coli*, and it is a possibility to induce a linker or spacer (such as an amino acid or amino acid sequence) region between the different fusion partners.

Uses

The invention also pertains to a method for producing an immunologic composition according to the invention, the method comprising preparing, synthesizing or isolating a polypeptide according to the invention, and solubilizing or dispersing the polypeptide in a medium for a diagnostic.

Diagnostic Protein

The invention also relates to a method of diagnosing TB caused by a virulent mycobacterium in an animal, including a human being, comprising intradermally injecting in the animal or transdermally applying to the animal, e.g. with a patch or plaster, a polypeptide or composition according to the invention, a positive skin response at the location of injection or applying being indicative of the animal having TB, and a negative skin response at the location of injection or applying being indicative of the animal not having TB.

It is also conceivable to contact a serum sample from a subject with a polypeptide or a composition of the invention, the demonstration of a binding between antibodies in the serum sample and the polypeptide being indicative of previous or ongoing infection.

The immunogenic composition used for diagnosing may comprise at least two (such as at least two, at least 3, at least 4, at least 5, at least 6, at least 7, at least 8, at least 9, at least 10 or more) different polypeptides or fusion polypeptides.

Diagnostic DNA

The nucleic acid probes encoding the polypeptide of the invention can be used in a variety of diagnostic assays for detecting the presence of pathogenic organisms in a given sample.

A method of determining the presence of mycobacterial nucleic acids in an animal, including a human being, or in a sample, comprising administering a nucleic acid fragment of the invention to the animal or incubating the sample with the nucleic acid fragment of the invention or a nucleic acid fragment complementary thereto, and detecting the presence of hybridized nucleic acids resulting from the incubation (by using the hybridization assays which are well-known in the art), is also included in the invention. Such a method of diagnosing TB might involve the use of a composition comprising at least a part of a nucleotide sequence as defined above and detecting the presence of nucleotide sequences in a sample from the animal or human being to be tested which hybridize with the nucleic acid fragment (or a complementary fragment) by the use of PCR technique.

FIGURE LEGEND

FIG. 1: Epitope mapping of Rv2653. Synthetic peptides 18-20 mer spanning the whole protein were tested one by one for recognition by PBMC from 6 TB patients (top) and 30 BCG vaccinated healthy controls (bottom). Each dot represents an individual donor, horizontal bars: mean value. Filled dots represent peptides with specific activity; blank dot represents peptides with substantial recognition in controls. All control persons were carefully asked for prior exposure to mycobacteria.

Figure 2:
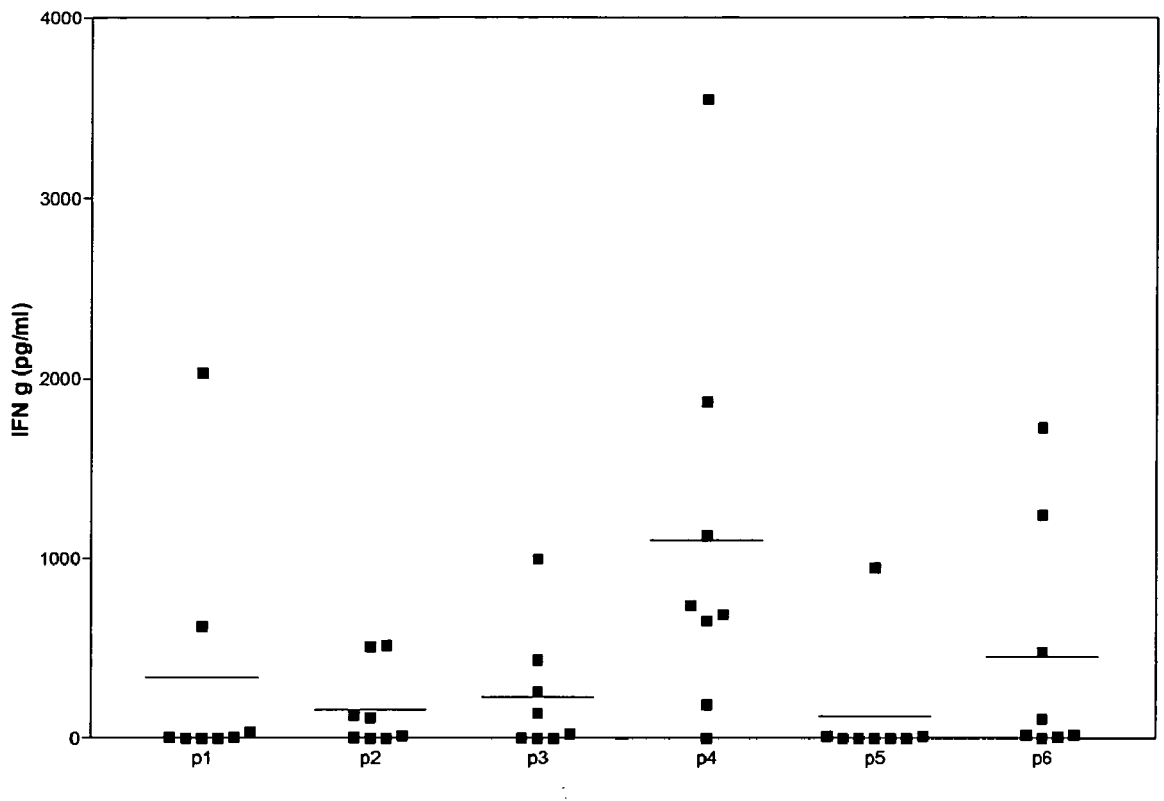
Figure 2:
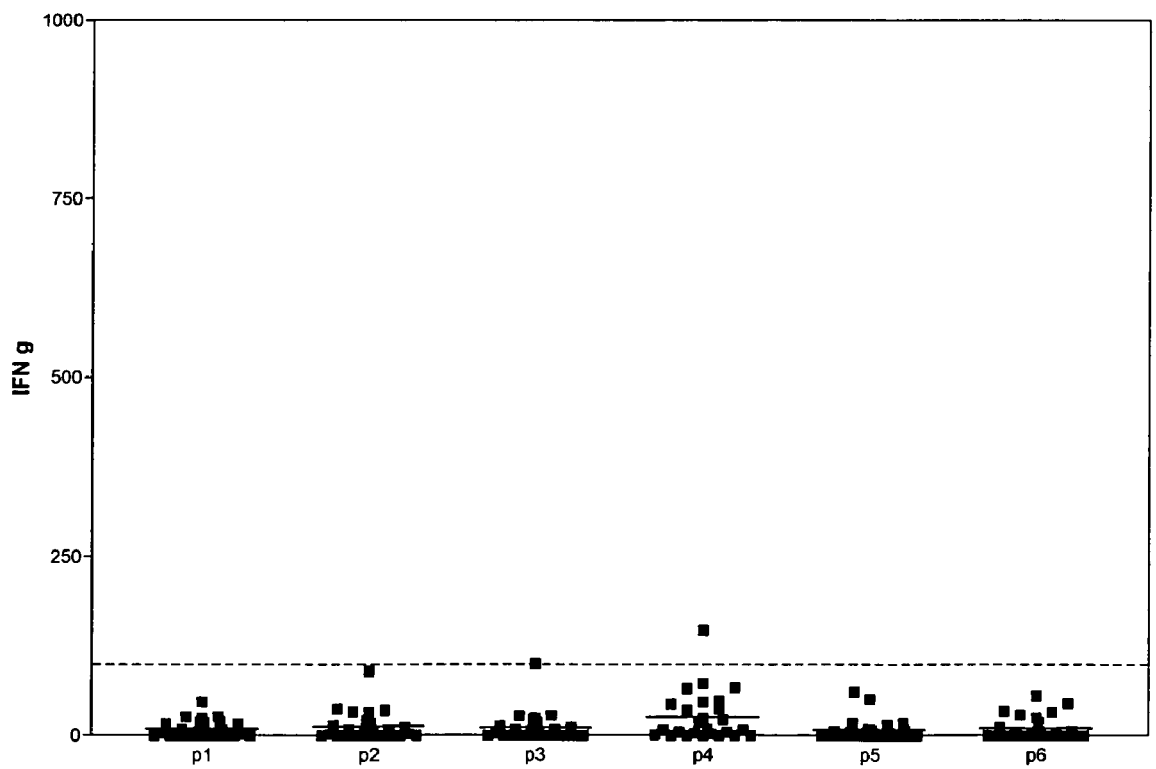

FIG. 2: Epitope mapping of Rv2654. Synthetic peptides 18-20 mer spanning the whole protein were tested one by one for recognition by PBMC from 8 TB patients (top) and 26 BCG vaccinated healthy controls (bottom). Each dot represents an individual donor. Filled dots represent peptides with specific activity; all peptides seem to be specific. All control persons were carefully asked for prior exposure to mycobacteria.

Figure 3:
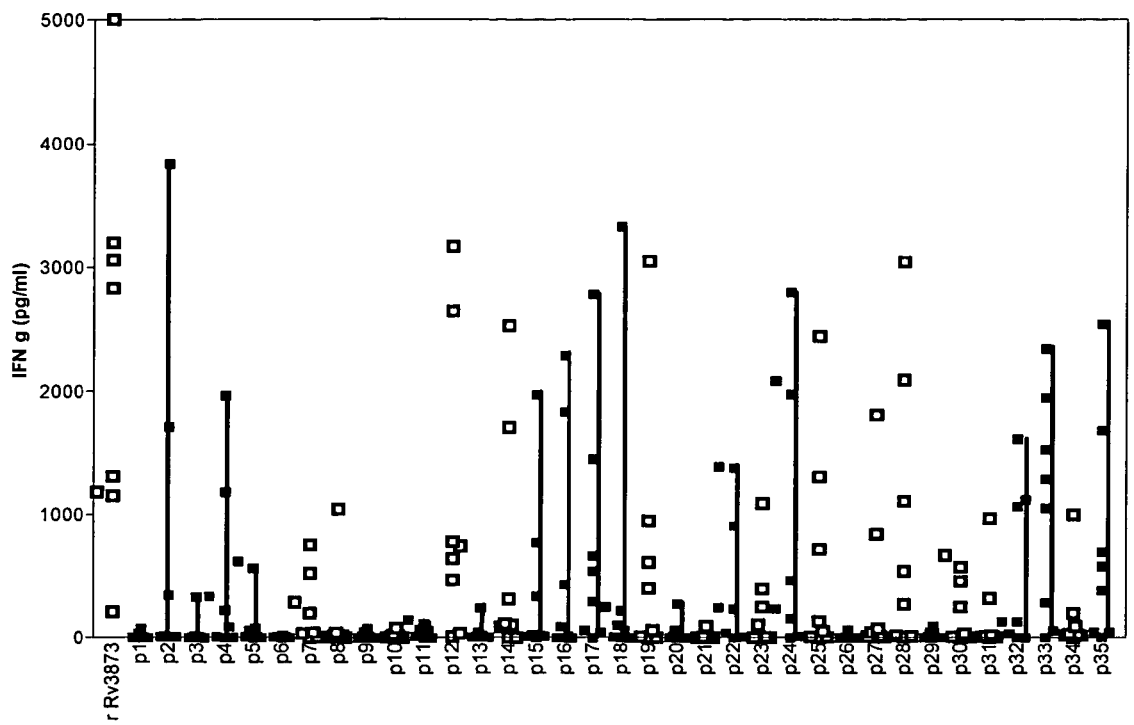
Figure 3:
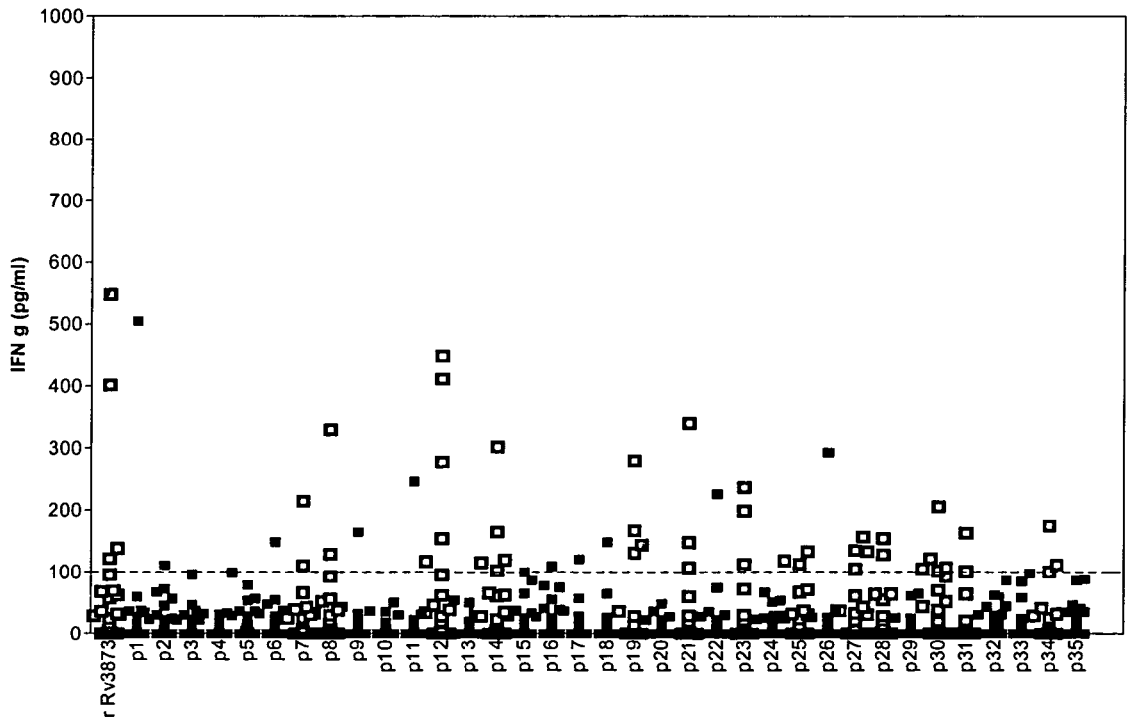

FIG. 3: Epitope mapping of Rv3873. Synthetic peptides 18-20 mer spanning the whole protein were tested one by one for recognition by PBMC from 8 TB patients (top) and 28 BCG vaccinated healthy controls (bottom). Each dot represents an individual donor. Filled dots represent peptides with specific activity; blank dot represents peptides with substantial recognition in controls. All control persons were carefully asked for prior exposure to mycobacteria.

Figure 4:
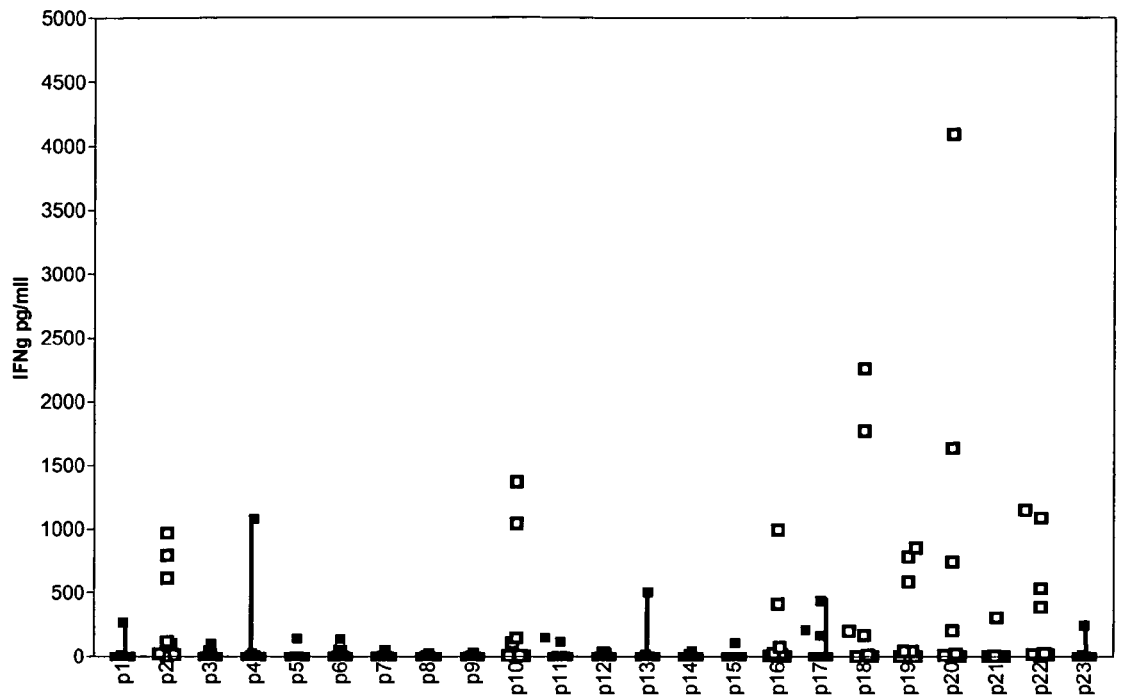
Figure 4:
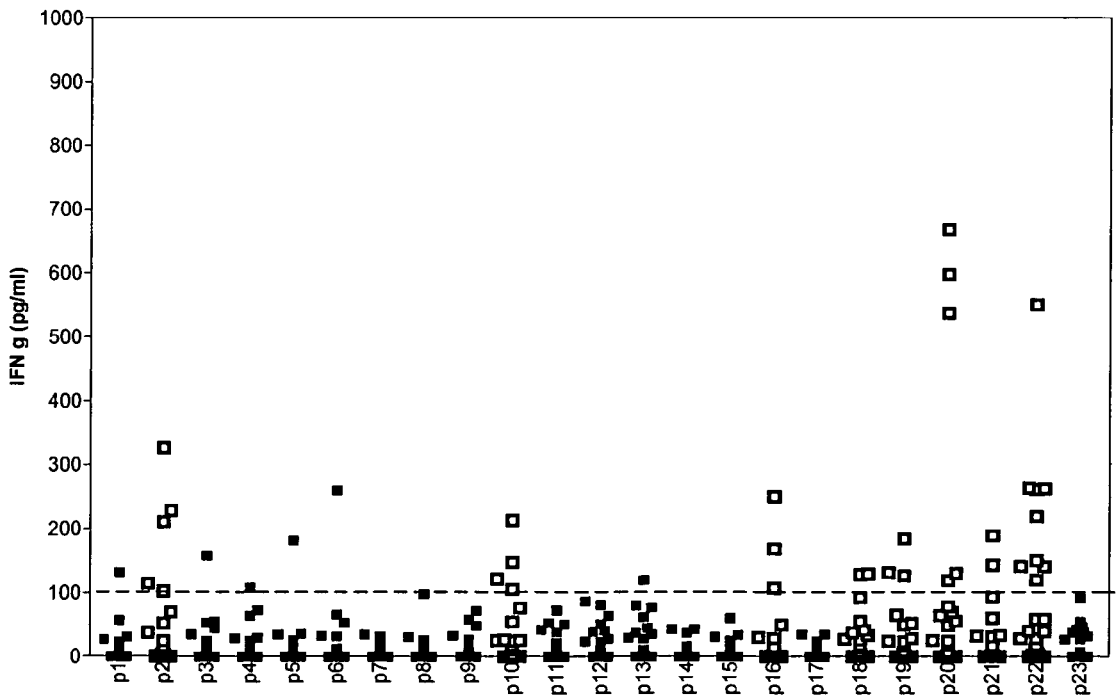

FIG. 4: Epitope mapping of Rv3878. Synthetic peptides 18-20 mer spanning the whole protein were tested one by one for recognition by PBMC from 8 TB patients (top) and 27 BCG vaccinated healthy controls (bottom). Each dot represents an individual donor. Filled dots represent peptides with specific activity; blank dot represents peptides with substantial recognition in controls. All control persons were carefully asked for prior exposure to mycobacteria.

Figure 5:
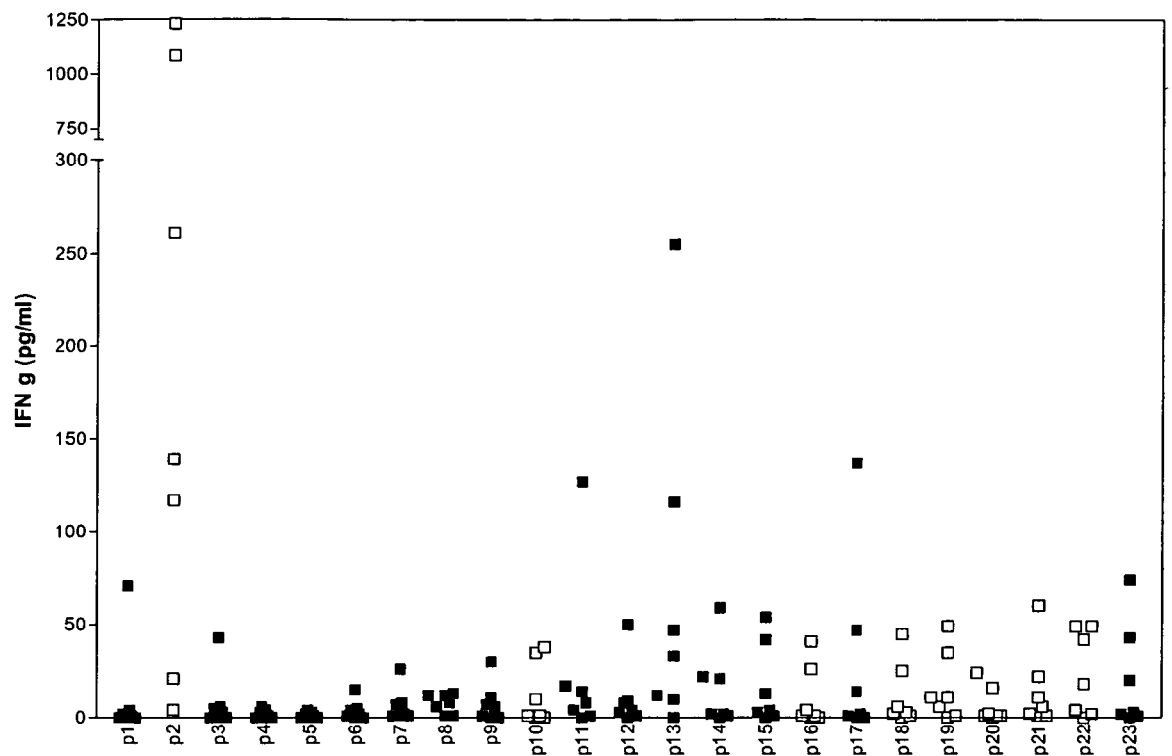

FIG. 5: Epitope mapping of Rv3878 using T cell lines. Synthetic peptides 18-20 mer spanning the whole protein were tested one by one for recognition by 7 T cell lines derived from TB patients. Each dot represents an individual T cell line. Filled dots represent peptides with specific activity; blank dot represents peptides with substantial recognition in controls.

EXAMPLE 1

Assay Conditions

PBMC were obtained from healthy BCG vaccinated donors with no history of contact to *M. tuberculosis* and from TB patients with microscopy- or culture-proven infection. Blood samples were drawn from TB patients 0-6 months after diagnosis. PBMC were freshly isolated by gradient centrifugation of heparinized blood on Lymphoprep (Nycomed, Oslo, Norway) and stored in liquid nitrogen until use. The cells were resuspended in complete RPMI 1640 medium (Gibco BRL, Life Technologies) supplemented with 1% penicillin/streptomycin (Gibco BRL, Life Technologies), 1% non-essential-amino acids (FLOW, ICN Biomedicals, CA, USA), and 10% heat-inactivated normal human AB serum (NHS). The viability and number of the cells were determined by Nigrosin staining.

PBMC cell cultures were established in triplicates with $1.25 \times 10^5$ PBMCs in 100 µl in microtitre plates (Nunc, Roskilde, Denmark) and stimulated with 5 µg/ml PPD, peptide pools spanning the entire length of the four proteins and CFP 10 in concentrations of 10 ug/ml.

Cell cultures with no antigen were included as negative control and phytohaemagglutinin (PHA) was used as positive control (results not shown). Cell cultures were incubated for 5 days at 37° C. (5% $CO_2$, 95% air) and supernatants were harvested for cytokine analysis.

The cytokine Interferon-γ (IFN-γ) was detected with a standard sandwich ELISA technique using a commercially available pair of monoclonal antibodies (Endogen, MA, US) and used according to the manufacturer's instruction. Recombinant IFN-γ (Endogen, MA, US) was used as a standard.

The chosen overlapping peptides (18 or 20 mers) from the four proteins Rv 2654 (RD 11), Rv 2653 (RD 11), Rv 3873 (RD 1) and Rv 3878 (RD 1) were synthesized by standard solid-phase methods at Schafer-N, Copenhagen, Denmark.

The peptides were purified by reverse phase HPLC. Purified peptides were lyophilized and stored dry until reconstitution in PBS.

EXAMPLE 2

Selection of Immunogenic Antigens

We have screened a large proportion (more than 70) of the ORF's deleted from BCG and only a few (approximately 10) of them are immunoreactive. The ORF's were tested for immunoreactivity using either isolated PBMC from TB patients or using T-cell lines derived from TB patients.

In Table 1 the results from 10 deleted ORF's are shown. These results illustrates the fact that not all RD proteins are immunoreactive when tested with sensitised lymphocytes, and none of these 10 example antigens is recognized by the T-cells.

TABLE 1

| RD region | Antigen | Line 1 | Line 2 | Line 3 | Line 4 | Line 5 |
|---|---|---|---|---|---|---|
|  | Non | 6 | 1 | 1 | 4 | 0 |
|  | PHA | 3313 | 1750 | 2033 | 2388 | 1127 |
| RD4 | Rv 0221 | 3 | 1 | 0 | 5 | 97 |
| RD4 | Rv 0223 | 1 | 6 | 1 | 4 | 5 |
| RD10 | Rv 1256 | 0 | 2 | 2 | 9 | 11 |
| RD3 | Rv 1574 | 2 | 0 | 2 | 39 | 0 |
| RD3 | Rv 1580 | 26 | 5 | 0 | 22 | 0 |
| RD15 | Rv 1970 | 5 | 1 | 0 | 0 | 0 |
| RD2 | Rv 1982 | 0 | 0 | 3 | 2 | 6 |
| RD12 | Rv 2074 | 0 | 41 | 2 | 2 | 5 |
| RD5 | Rv 3119 | 14 | 0 | 3 | 7 | 16 |
| RD11 | Rv 3426 | 19 | 2 | 7 | 4 | 7 |

Table 1. Examples of antigens belonging to the RD regions tested in T-cell lines derived from TB patients. Results are giving in pg/ml IFN gamma. Positive results are marked with bold.

As seen in Table 1, the antigens were produced as presented elsewhere and tested in T-cell lines derived from TB patients in the following manner. Peripheral blood mononuclear cells (PBMC) were obtained from culture or microscopy proven TB patients PMBC were incubated at $1-2 \times 10^6$ cells/well in 24-well plates (Nunc, Roskilde, Denmark) in the presence of ST-CF at 5 μg/ml for six days, then expanded with rIL-2. The T cell lines were then frozen and stored in liquid nitrogen. Five cell lines were generated using *M. tuberculosis* short-term culture filtrate (ST-CF). Only T cell lines that were *M. tuberculosis*-reactive, i.e. responding to *M. tuberculosis* sonicate or PPD (tuberculin RT23; Statens Serum Institute, Copenhagen, Denmark), but not to tetanus toxoid, were used in the present study. For the analysis of antigen specific responses, T cell lines ($15 \times 10^3$/well) were incubated with irradiated autologous PBMC ($50 \times 10^3$/well), with or without antigen (PHA at 2 μg/ml, ST-CF at 5 μg/ml, recombinant antigen at 5 μg/ml, in a total volume of 200 μl/well in triplicate in 96-well flat-bottomed microtiter plates. The level of IFN-gamma release was determined after 4 days of incubation.)

Based on the initial screening results we selected the four best RD proteins and tested these in a limited panel of PBMC derived from culture confirmed TB patients. As demonstrated in Table 2 all these proteins were recognized by two or more donors.

TABLE 2

| RD region | Antigen | Donor 1 | Donor 2 | Donor 3 | Donor 4 | Donor 5 |
|---|---|---|---|---|---|---|
| RD11 | Rv2653 peptide pool | 9977 | 1704 | 147 | 5527 | 580 |
| RD11 | Rv2654 peptide pool | 333 | 665 | 70 | 43 | 0 |
| RD1 | Rv3873 recombinant protein | 1149 | 5000 | 256 | 3121 | 604 |
| RD1 | Rv3878 recombinant protein | 438 | 20 | 62 | 2034 | 413 |

Table 2: Antigens belongigng to the RD regions tested in PBMC derived from TB patients. These four antigens are all recognized by two or more donors. Assay conditions were as described in Example 1. Results are giving in pg/ml IFN gamma. Positive results are marked with bold.

To demonstrate the diagnostic potential of these proteins in a diagnostic setting they were tested in a larger panel of PBMC from culture confirmed TB patients and from BCG vaccinated control persons. The results confirm that these antigens are frequently recognised by TB patients, but results also reveals some recognition in the BCG vaccinated controls, meaning that the proteins must contain regions with unspecific activity (Table 3).

TABLE 3

| | | | | | Recognition >200 pg IFN | |
|---|---|---|---|---|---|---|
| RD region | Antigen | MW | pI | Gene | Patients | Controls |
| 1 | TB 37.6 | 37.3 | 4.0 | Rv 3873 | 8/19  42% | 3/13  23% |
| 1 | TB 27.4 | 27.4 | 3.88 | Rv 3878 | 10/19  53% | 10/36  28% |
| 11 | TB 12.3 | 12.3 | 9.09 | Rv 2653 | 12/27  44% | 10/17  59% |
| 11 | TB 7.7 | 4.86 | 9.09 | Rv 2654 | 9/18  50% | 1/39  2% |

Table 3: 4 new proteins belonging to the RD regions tested in PBMC derived from TB patients and BCG vaccinated healthy controls. All control persons were carefully asked for prior exposure to mycobacteria. The proteins were tested in the following form: TB 37.6 were tested as recombinant protein, TB 27.4 were tested as pools of overlapping peptides spanning the entire length of the protein; best performing of 4 pools are shown, TB 12.4 were tested as pools of overlapping peptides spanning the entire length of the protein; best performing of 2 pools are shown and TB 7.7 were tested as a single pool of overlapping peptides spanning the entire length of the protein.

Recognition of the antigens was determined in terms of IFN gamma release (pg/ml) after antigen stimulation in 5 days. (Recognition: numbers of patients that recognize the protein/numbers of patients tested)

This screening of the ORF's from the RD regions resulted in a selection of four promising antigens with potential to be included in a specific diagnostic reagent for detection of TB infection. These antigens are: Rv 2653 (RD11), Rv 2654 (RD11), Rv 3873 (RD1) and Rv 3878 (RD1).

EXAMPLE 3

Definition of Specific Regions in the Selected Antigens

The antigens were initially tested for recognition by PBMC from TB patients and controls. Even though the four new selected proteins were chosen from the RD regions of the M. tub. genome, we most surprisingly found substantial recognition of two of the antigens by PBMC from BCG vaccinated healthy controls with no known contact to mycobacteria. All participants in the control panel were carefully asked for prior exposure to mycobacteria, occupational or otherwise, and all had only one known exposure: the BCG vaccination.

As seen in Table 3 the immunological testing of recombinant Rv 3873 (the full length protein), Rv 3878 peptide pools spanning the whole protein and Rv 2653 peptide pools spanning the whole protein gave rise to substantial (between 23% and 59%) recognition in terms of IFN-g release in samples of healthy BCG vaccinated persons.

To further investigate this phenomena of cross reactivity, synthetic peptides 18-20 mer spanning the full length of all of the four proteins were produced. All these single peptides were tested for recognition by PBMC from TB patients and from healthy BCG vaccinated controls, thereby making a fine epitope and specificity mapping of the four proteins at the epitope level.

The results of this fine epitope and specificity mapping of the four proteins are shown in FIG. 1 to FIG. 4. All figures display in the top panel the recognition of the single peptides by PBMC from TB patients, and in the bottom panel the recognition of the single peptides by PBMC from healthy BCG vaccinated donors. As seen three out of the four tested antigens contains regions, which are recognised recognized substantially by PBMC from healthy control donors. These regions are not suitable for a cocktail or fusion protein of epitopes to be used in a diagnostic test.

These data clearly demonstrates that it is not possible on the basis of the genomic data alone to predict if an ORF from an RD region is immunogenic and which part of an antigen that are recognized by *M. tuberculosis* infected persons and not by BCG vaccinated healthy controls.

On the basis of these results we selected the peptides that are specific for infection with *M. tuberculosis*. The selection criteria for the peptides to be included in a CMI based TB diagnostic was: The single peptide should not give rise to more than 100 pg/ml IFN gamma when tested in a panel of BCG vaccinated control donors (one outliner allowed). The following peptides were selected:

TABLE 4

| PROTEIN | PEPTIDE NUMBER |
|---|---|
| RV 2653 | 1, 2, 3, 7, 8, 9, 10 |
| RV 2654 | 1, 2, 3, 4, 5, 6 |
| RV 3873 | 1, 2, 3, 4, 5, 6, 9, 10, 11, 13, 15, 16, 17, 18, 20, 22, 24, 26, 29, 32, 33, 35 |
| RV 3878 | 1, 3, 4, 5, 6, 7, 8, 9, 11, 12, 13, 14, 15, 17, 23 |

Table 4: List of the selected peptides as potential components in a future CMI based immunological TB diagnostic. Selection criteria: Peptides spanning the whole length of the 4 new proteins were tested one by one with PBMC from 27-30 BCG vaccinated healthy controls.
All peptides giving more than 100 pg/ml IFN gamma in a stimulation assay were taken out (one outliner allowed/peptide).

Sequence list for the selected peptides:

| Protein | Peptide | Sequence | SEQ ID NO. |
|---|---|---|---|
| Rv2653 | P1 | MTHKRTKRQPAIAAGLNA | 1 |
| | P2 | AIAAGLNAPRRNRVGRQH | 2 |
| | P3 | RNRVGRQHGWPADVIPSAE | 3 |
| | P7 | TSHEIDDDTAELALLSMH | 4 |
| | P8 | ELALLSMHLDDEQRRLEA | 5 |
| | P9 | DEQRRLEAGMKLGWHPYH | 6 |
| | P10 | MKLGWHPYHFPDEPDSKQ | 7 |
| Rv2654 | P1 | MSGHALAARTLLAAADEL | 8 |
| | P2 | AADELVGGPPVEASAAAL | 9 |
| | P3 | ASAAALAGDAAGAWRTAA | 10 |
| | P4 | AWRTAAVELARALVRAVA | 11 |
| | P5 | LVRAVAESHGVAAVLFAA | 12 |
| | P6 | VLFAATAAAAAVDRGDPP | 13 |
| Rv3873 | P1 | MLWHAMPPELNTARLLMAG | 14 |
| | P2 | ARLMAGAGPAPMLAAAAG | 15 |
| | P3 | PMLAAAAGWQTLSAALDA | 16 |
| | P4 | TLSAALDAQAVELTARLN | 17 |
| | P5 | VELTARLNSLGEAWTGGG | 18 |
| | P6 | GEAWTGGGSDKALAAATP | 19 |
| | P9 | KTRAMQATAQAAAYTQAM | 20 |
| | P10 | AAYTQAMATTPSLPEIAA | 21 |
| | P11 | LPEIAANHITQAVLTATN | 22 |
| | P13 | NTIPIALTEMDYFIRMWN | 23 |
| | P15 | AALAMEVYQAETAVNTLF | 24 |
| | P16 | ETAVNTLFEKLEPMASIL | 25 |
| | P17 | LEPMASILDPGASQSTTN | 26 |
| | P18 | GASQS1TNPIFGMPSPGS | 27 |
| | P20 | PVGQLPPAATQTLGQLGE | 28 |
| | P22 | GPMQQLTQPLQQVTSLFS | 29 |
| | P24 | GGTGGGNPADEEAAQMGL | 30 |
| | P26 | TSPLSNHPLAGGSGPSAG | 31 |
| | P29 | GGSLTRTPLMSQLIEKPV | 32 |
| | P32 | ATGGAAPVGAGAMGQGAQ | 33 |
| | P33 | AMGQGAQSGGSTRPGLVA | 34 |
| | P35 | AQEREEDDEDDWDEEDDW | 35 |
| Rv3878 | P1 | AEPLAVDPTGLSAAAAKLAG | 36 |
| | P3 | QPPAPLAVSGTDSVVAAINE | 37 |
| | P4 | SVVAAINETMPSIESLVSDG | 38 |

-continued

Sequence list for the selected peptides:

| Protein | Peptide | Sequence | SEQ ID NO. |
|---------|---------|----------|------------|
|  | P5 | IESLVSDGLPGVKAALTRTA | 39 |
|  | P6 | KAALTRTASNMNAAADVYAK | 40 |
|  | P7 | AAADVYAKTDQSLGTSLSQY | 41 |
|  | P8 | LGTSLSQYAFGSSGEGLAGV | 42 |
|  | P9 | SGEGLAGVASVGGQPSQATQ | 43 |
|  | P11 | PVSQVTTQLGETAAELAPRV | 44 |
|  | P12 | AAELAPRVVATVPQLVQLAP | 45 |
|  | P13 | PQLVQLAPHAVQMSQNASPI | 46 |
|  | P14 | MSQNASPIAQTISQTAQQAA | 47 |
|  | P15 | SQTAQQAAQSAQGGSGPMPA | 48 |
|  | P17 | AEKPATEQAEPVHEVTNDDQ | 49 |
|  | P23 | SPLAAPVDPSTPAPSTTTTL | 50 |

Furthermore the data shown in FIGS. 1-4 shows that certain regions of the proteins are very frequently recognized: for instance Rv 2654 peptide 4, and to lesser extent peptide 1 and 6; Rv 3873 peptide 15-18 and 2-5. For Rv 3878 the experiments using T cell lines (FIG. 5) indicates a region with peptide 11-15 and peptide 17 as very frequently recognized.

EXAMPLE 4

Diagnostic Performance of the Antigens

The peptides were pooled in the following manner for future testing:

| Protein | Pool name | Peptides in pool |
|---------|-----------|------------------|
| Rv 2653 | pool | p1, p2, p3, p7, p8, p9, p10 |
| Rv 2654 | pool | p1, p2, p3, p4, p5, p6 |
| Rv 3873 | pool A | p2, p3, p4, p5, p6 |
|  | pool B | p9, p10, p11 |
|  | pool C | p15, p16, p17, p18 |
|  | pool D | p22, p24, p29, p32, p33, p35 |
|  | pool E | p20, p26, p1, p13 |
| Rv 3878 | pool A: | p3, p4, p5, p6, p7, p8, p9 |
|  | pool B: | p11, p12, p13, p14, p15 |
|  | pool C: | p1, p23, p17 |

To test whether these peptides indeed have the potential to improve the sensitivity of the well known proteins CFP 10 and Esat 6 we tested the 4 peptide pools that looked most promising from the epitope mapping in a stimulation assay using PBMC from 15 TB patients with culture/microscopy proven TB and 29 BCG vaccinated healthy controls. The chosen pools were: Rv 2654 pool, Rv3873 pool A and Rv3873 pool C. Furthermore a small region of Rv 3878 B (peptide 11+13) was tested in 20 other patients and 13 BCG vaccinated controls.

The pools were tested in the concentration found optimal for the individual pool, when tested in responding donors otherwise test conditions were as described in example 1.

On the basis of these results the diagnostic performance of each individual tested peptide pool and recombinant CFP 10 and Esat 6 were calculated in Table 5. Cut off was determined from a ROC curve [Zweigh 1993] analysis based on test results using the individual peptide pools to stimulate PBMC from 15 TB patients and 30 BCG vaccinated healthy controls, aiming at a specificity level of 97%.

TABLE 5

| Antigen | Recognition | Sensitivity | Cut off (pg/ml) |
|---------|-------------|-------------|-----------------|
| Recombinant CFP 10 | 10/15 | 67% | 94 |
| Recombinant Esat 6 | 9/15 | 60% | 80 |
| Rv 2654 peptide pool | 5/15 | 33% | 53 |
| Rv 3873 peptide pool A | 5/15 | 33% | 73 |
| Rv 3873 peptide pool C | 1/15 | 7% | 212 |
| Rv 3878 peptide 11 + 13 | 9/20 | 45% | 98 |

Table 5: PBMC from 15 culture proven TB patients were tested with a selection of the new *M. tuberculosis* specific epitopes and with CFP 10 and Esat 6. Futhermore Rv3878 peptide 11 + 13 were tested in 20 other patients and 13 BCG vaccinated controls. Assay conditions are as described in Example 1.
(Recognition: numbers of patients that recognize the protein/numbers of patients tested)

To demonstrate the increase in sensitivity obtained by adding new specific epitopes to CFP10 and Esat 6 in a diagnostic setting, we compared the individual responses to some of the newly identified peptide pools (Table 6). Notice that PBMC from two of the donors (donor 9 and donor 11) do not recognise CFP 10 and Esat 6, but recognises recognizes one or two of the new antigens. These data clearly indicates that it is possible to increase the sensitivity of the assay using other specific epitopes in addition to CFP 10 and Esat 6.

| Donor | CFP10 | Esat6 | 2654 Pool | 3873 Pool A | 3873 Pool C |
|-------|-------|-------|-----------|-------------|-------------|
| 1 |  | ■ |  |  |  |
| 2 | ■ | ■ |  |  |  |
| 3 | ■ | ■ |  | ■ |  |
| 4 | ■ | ■ |  |  |  |
| 5 |  | ■ |  |  |  |
| 6 | ■ |  |  |  |  |
| 7 | ■ |  |  |  |  |
| 8 |  | ■ |  |  |  |
| 9 |  |  |  | ■ |  |
| 10 |  |  | ■ |  |  |
| 11 |  |  | ■ | ■ |  |
| 12 | ■ | ■ | ■ | ■ | ■ |
| 13 | ■ | ■ |  |  |  |
| 14 | ■ |  | ■ |  |  |
| 15 | ■ | ■ | ■ |  |  |

Table 6: PBMC from 15 culture proven TB patients were tested with a selection of the new *M. tuberculosis* specific epitopes ad with CFP 10 and Esat 6. Assay conditions are as described in Example 1. Dark colour indicates recognition of the antigen above the cut off limit determined on the basis of ROC curve analysis of stimulation assay using PBMC from 30 healthy BCG vaccinated controls.

In order to increase the sensitivity of the diagnostic assay we combined the selected peptide pools and evaluated the diagnostic performance of these combinations as stated below:

| Antigen/combinations | Recognition | Sensitivity |
|----------------------|-------------|-------------|
| A: Esat 6 | 9/15 | 60% |
| B: CFP 10 | 10/15 | 67% |
| C: Esat 6 + CFP 10 | 12/15 | 80% |

-continued

| Antigen/combinations | Recognition | Sensitivity |
| --- | --- | --- |
| D: Esat 6 + CFP 10 + Rv3873 pool A | 13/15 | 87% |
| E: Esat 6 + CFP 10 + Rv3873 pool A + Rv2654 | 14/15 | 93% |

These results clearly demonstrates that addition of other specific epitopes to the already known specific antigens CFP 10 and Esat 6 can increase the sensitivity of a diagnostic assay based on cell mediated immune response. In this example the sensitivity was raised from 60% (using only Esat 6) to 93% using the proteins Esat 6, CFP 10, Rv2654 and Rv3873 pool A (peptide 2, 3, 4, 5 and 6).

The high sensitivity and specificity of the novel epitopes is also demonstrated using a new panel of TB patients and controls as shown in Table 7. These data confirm the ability to increase the sensitivity of the diagnostic cocktail without compromising the specificity by combining the novel specific peptides in combination with CFP10 and ESAT6. The data in Table 7 furthermore demonstrated that this diagnostic cocktail can be used to diagnose an *M. tuberculosis* infection in latent infected individuals (a subclinical infection) as well as in individuals with active TB.

TABLE 7

Diagnostic performance of the novel peptide mixtures and in combination with ESAT6 and CFP10 in another panel of Danish TB patients and healthy controls.

| Antigen | Sensitivity[a,b] Latent TB (n = 13) | Sensitivity[a,b] Active TB (n = 8) | Sensitivity[a,b] TB infection (n = 21) | Specificity[c] (n = 22) |
| --- | --- | --- | --- | --- |
| Rv2654 | [6] 46 [19-53] | [3] 38 [4-71] | [9] 42 [22-64] | 100 [100-100] |
| Rv3873A | [4] 31 [6-56] | [4] 50 [15-85] | [8] 38 [17-59] | 95 [87-104] |
| Rv3878B | [8] 62 [35-88] | [4] 50 [15-85] | [12] 57 [36-78] | 100 [100-100] |
| Combination: ESAT 6 + CFP 10 + Rv2654 + Rv3873A + Rv3878B | [12] 92 [78-107] | [7] 88 [65-110] | [19] 90 [78-103] | 95 [87-104] |

[a]Cut off determined by ROC curve analysis: ESAT 6; 94 pg/ml, CFP 10; 80 pg/ml, Rv2654; 53 pg/ml, Rv3873 A; 73 pg/ml and Rv3878 B; 38 pg/ml.
[b]Sensitivity: responding *M. tuberculosis* infected individuals out of all infected individuals tested. [number], percentage, [95% confidence interval; percentage].
[c]Specificity: percentage of negative individuals out of all [22] BCG vaccinated individuals categorised as having low risk of exposure to *M. tuberculosis* in a contact tracing investigation.

The invention will now be further described by the following numbered paragraphs:

1. A composition comprising at least two (such as at least two, at least 3, at least 4, at least 5, at least 6, at least 7, at least 8, at least 9, at least 10 or more) amino acid sequences independently selected from the group consisting of:
a) a fragment of any of: Rv2654, Rv2653, or Rv3873; and/or
b) an amino acid sequence having at least 70% (such as at least 75%, at least 80%, at least 85%, at least 90% or at least 95%) sequence identity to a fragment in a).

2. A composition according to paragraph 1, in which the at least two amino acid sequences are independently selected from the group consisting of:
a) an immunogenic fragment (such as a fragment comprising an epitope, e.g. T-cell epitope) of any of: Rv2654, Rv2653 or Rv3873; and/or
b) an immunogenic amino acid sequence (such as a sequence comprising an epitope, e.g. T-cell epitope) having at least 70% sequence identity to any one of the sequences in (a).

3. A composition according to any of paragraphs 1-2, further comprising an amino acid sequence selected from the group consisting of:
a) a fragment of Rv3878; and/or
b) an amino acid sequence having at least 70% (such as at least 75%, at least 80%, at least 85%, at least 90% or at least 95%) sequence identity to a fragment in a).

4. A composition according to any one of paragraphs 1-4, further comprising at least one amino acid sequence (such as 2, 3, 4, 5, 6, 7, 8, 9, or more) selected from the group consisting of: ESAT6, CFP10 and Rv1980, and subsequences thereof (such as fragments comprising an epitope).

5. A composition comprising at least three (such as at least 3, at least 4, at least 5, at least 6, at least 7, at least 8, at least 9, at least 10 or more) amino acid sequences independently selected from the group consisting of:
a) a fragment of any of: Rv2654, Rv2653, Rv3873 or Rv3878; and/or
b) an amino acid sequence having at least 70% (such as at least 75%, at least 80%, at least 85%, at least 90% or at least 95%) sequence identity to a fragment in a).

6. A composition according to paragraph 5, in which the at least three amino acid sequences are independently selected from the group consisting of:
a) an immunogenic fragment (such as a fragment comprising an epitope, e.g. T-cell epitope) of any of: Rv2654, Rv2653, Rv3873 or Rv3878; and/or
b) an immunogenic amino acid sequence (such as a sequence comprising an epitope, e.g. T-cell epitope) having at least 70% sequence identity to any one of the sequences in (a).

7. A composition according to any one of paragraphs 5-6, further comprising at least one amino acid sequence (such as 2, 3, 4, 5, 6, 7, 8, 9, or more) selected from the group consisting of: ESAT6, CFP10 and Rv1980, and subsequences thereof (such as fragments comprising an epitope).

8. A composition according to paragraphs 1-7 comprising at least one amino acid sequence (such as 2, 3, 4, or 5) of Rv3873 selected from the group consisting of: SEQ ID NOs: 15, 16, 17, 18 and 19.

9. A composition according to paragraphs 1-7 comprising at least one amino acid sequence (such as 2, 3, or 4) of Rv3873 selected from the group consisting of: SEQ ID NOs: 24, 25, 26 and 27.

10. A composition according to paragraph 3-7 comprising at least one amino acid sequence (such as 2, 3, 4, or 5) of Rv3878 selected from the group consisting of: SEQ ID NOs: 44, 45, 46, 47 and 48.

11. A composition according to paragraph 1-7 comprising at least one amino acid sequence (such as 2, 3, 4, 5 or 6) of Rv2654 selected from the group consisting of: SEQ ID NOs: 8, 9, 10, 11, 12, 13.

12. A composition according to paragraph 11 comprising SEQ ID NO: 11.

13. A composition according to any of the preceding paragraphs comprising the amino acid sequence of full length Rv2654.

14. A composition according to any of the preceding paragraphs, wherein all amino acid sequences are present in the composition as separate entities.

15. A composition according to any of the preceding paragraphs, wherein at least two (such as at least 3, at least 4, at least 5, at least 6, at least 7, at least 8) of the amino acid sequences are fused, optionally via linkers or spacers (such as an amino acid or an amino acid sequence).

16. A composition according to any one of the preceding paragraphs for use as a pharmaceutical or diagnostic reagent.

17. Use of a composition according to any of the preceding paragraphs for the preparation of a pharmaceutical composition, e.g. for diagnosis of tuberculosis caused by virulent mycobacteria, e.g. by *Mycobacterium tuberculosis, Mycobacterium africanum* or *Mycobacterium bovis*.

18. A diagnostic tool comprising a composition according to any of paragraphs 1-15

19. A CMI diagnostic tool comprising a composition according to any of paragraphs 1-15

20. A method for diagnosing previous or ongoing infection with a virulent mycobacterium, e.g. by *Mycobacterium tuberculosis, Mycobacterium africanum* or *Mycobacterium bovis*, said method comprising contacting a sample (such as cells isolated from e.g.: a bodily fluid such as blood, the spleen, the liver or the lung) with a composition according to any of paragraphs 1-15 in order to detect a positive reaction, such as cell proliferation or release of IFN-gamma or other cytokines such as IL-12, TNF-alpha, IL-4, IL-5, IL-10, IL-6, TGF-beta.

21. A method of diagnosing tuberculosis caused by virulent mycobacteria, e.g. by *Mycobacterium tuberculosis, Mycobacterium africanum* or *Mycobacterium bovis*, in an animal, including a human being, comprising intradermally injecting, in the animal, or applying on the animals skin a composition according to any of paragraphs 1-15, a positive skin response at the location of injection or application being indicative of the animal having tuberculosis, and a negative skin response at the location of injection or application being indicative of the animal not having tuberculosis.

22. Use of a composition according to any of paragraphs 1-15 for preparing a reagent for performing a skin test on an animal, including a human being, the skin test being intradermally injecting, in the animal, or applying on the animals skin a composition according to any of paragraphs 1-15, a positive skin response at the location of injection or application being indicative of the animal having tuberculosis, and a negative skin response at the location of injection or application being indicative of the animal not having tuberculosis.

23. A polypeptide selected from the group consisting of:
a) a fragment of any of: Rv2654, Rv2653, Rv3873 or Rv3878; and
b) an amino acid sequence having at least 70% (such as at least 75%, at least 80%, at least 85%, at least 90% or at least 95%) sequence identity to a fragment in a).

24. A polypeptide which comprises an amino acid sequence selected from the group consisting of
a) SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50; and
b) an amino acid sequence having at least 70% (such as at least 75%, at least 80%, at least 85%, at least 90% or at least 95%) sequence identity to an amino acid sequence in a), with the proviso that full-length Rv2654, Rv2653, Rv3873 and Rv3878 are excluded.

25. A polypeptide according to paragraph 24 which in its amino acid sequence comprises at least 2 (such as at least 3, at least 4, at least 5, at least 6, at least 7, at least 8, at least 9, at least 10) amino acid sequences independently selected from the group consisting of
a) SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50; and
b) an amino acid sequence having at least 70% (such as at least 75%, at least 80%, at least 85%, at least 90% or at least 95%) sequence identity to an amino acid sequence in a).

26. A polypeptide according to paragraph 25, in which the amino acid sequences are coupled via a linker or spacer (such as an amino acid or an amino acid sequence).

27. A polypeptide according to any of paragraphs 24-26, comprising ESAT6 (or an epitope thereof), and/or CFP10 (or an epitope thereof) and/or Rv1980 (or an epitope thereof) and at least one fragment(s) (comprising an epitope) of Rv3873, preferably selected from the group consisting of: SEQ ID NOs: 15, 16, 17, 18, and 19 or from the group consisting of SEQ ID Nos: 24, 25, 26 and 27, or/and of Rv3878, preferably selected from the group consisting of: SEQ ID NOs: 44, 45, 46, 47 and 48, or/and of Rv2654, preferably selected from the group consisting of: SEQ ID NOs: 8, 9, 10, 11, 12, and 13.

REFERENCES

1. Andersen, P., M. E. Munk, J. M. Pollock, and T. M. Doherty. 2000. Specific immune-based diagnosis of tuberculosis [In Process Citation]. Lancet. 356:1099-104.
2. Arend, S. M., P. Andersen, K. E. van Meijgaarden, R. L. Skjot, Y. W. Subronto, J. T. van Dissel, and T. H. Ottenhoff. 2000. Detection of active tuberculosis infection by T cell responses to early-secreted antigenic target 6-kDa protein and culture filtrate protein 10. J Infect Dis. 181:1850-4.
3. Arend, S. M., A. C. Engelhard, G. Groot, K. de Boer, P. Andersen, T. H. Ottenhoff, and J. T. van Dissel. 2001a. Tuberculin skin testing compared with T-cell responses to *Mycobacterium tuberculosis*-specific and nonspecific antigens for detection of latent infection in persons with recent tuberculosis contact. Clin Diagn Lab. Immunol. 8:1089-96.
4. Arend, S. M., T. H. Ottenhoff, P. Andersen, and J. T. van Dissel. 2001b. Uncommon presentations of tuberculosis: the potential value of a novel diagnostic assay based on the

*Mycobacterium tuberculosis*-specific antigens ESAT-6 and CFP-10. Int. J. Tuberc. Lung Dis. 5:680-6.
5. Behr, M. A., M. A. Wilson, W. P. Gill, H. Salamon, G. K. Schoolnik, S. Rane, and P. M. Small. 1999. Comparative genomics of BCG vaccines by whole-genomeDNA microarray. Science. 284:1520-1523.
6. Brock, I., M. E. Munk, A. Kok-Jensen, and P. Andersen. 2001. Performance of whole blood IFN-gamma test for tuberculosis diagnosis based on PPD or the specific antigens ESAT-6 and CFP-10. Int J Tuberc Lung Dis. 5:462-7.
7. Lalvani, A., A. A. Pathan, H. Durkan, K. A. Wilkinson, A. Whelan, J. J. Deeks, W. H. Reece, M. Latif, G. Pasvol, and A. V. Hill. 2001a. Enhanced contact tracing and spatial tracking of *Mycobacterium tuberculosis* infection by enumeration of antigen-specific T cells. Lancet. 357:2017-21.
8. Lalvani, A., A. A. Pathan, H. McShane, R. J. Wilkinson, M. Latif, C. P. Conlon, G. Pasvol, and A. V. Hill. 2001b. Rapid detection of *Mycobacterium tuberculosis* infection by enumeration of antigen-specific T cells. Am J Respir Crit Care Med. 163:824-8.
9. Lein, A. D., C. F. von Reyn, P. Ravn, C. R. Horsburgh, Jr., L. N. Alexander, and P. Andersen. 1999. Cellular immune responses to ESAT-6 discriminate between patients with pulmonary disease due to *Mycobacterium avium* complex and those with pulmonary disease due to *Mycobacterium tuberculosis*. Clin Diagn Lab Immunol. 6:606-9.
10. Munk, M. E., S. M. Arend, I. Brock, T. H. Ottenhoff, and P. Andersen. 2001. Use of ESAT-6 and CFP-10 antigens for diagnosis of extrapulmonary tuberculosis. J Infect Dis. 183:175-6.
11. Ravn, P., A. Demissie, T. Eguale, H. Wondwosson, D. Lein, H. Amoudy, A. S. Mustafa, A. K. Jensen, A. Holm, I. Rosenkrands, F. Oftung, J. Olobo, C. F. von-Reyn, and P. Andersen. 1999. Human T cell responses to the ESAT-6 antigen from *Mycobacterium tuberculosis*. J. Infect. Dis. 179:637-645.
12. Ulrichs, T., P. Anding, S. Porcelli, S. H. Kaufmann, and M. E. Munk. 2000. Increased numbers of ESAT-6- and purified protein derivative-specific gamma interferon-producing cells in subclinical and active tuberculosis infection. Infect Immun. 68:6073-6.
13. van Pinxteren, L. A., P. Ravn, E. M. Agger, J. Pollock, and P. Andersen. 2000. Diagnosis of tuberculosis based on the two specific antigens ESAT-6 and CFP10. Clin Diagn Lab Immunol. 7:155-60.
14. Vordermeier, H. M., A. Whelan, P. J. Cockle, L. Farrant, N. Palmer, and R. G. Hewinson. 2001. Use of synthetic peptides derived from the antigens ESAT-6 and CFP-10 for differential diagnosis of bovine tuberculosis in cattle. Clin Diagn Lab Immunol. 8:571-8.
15. WHO. 2000. Tuberculosis, Fact Sheet No. 104. WHO Homepage, www.who.org.
16. Zweig, M. H, Campbell, G. Receiver-operating characteristic (ROC) plots: a fundamental evaluation tool in clinical medicine. 1993. Clin Chem. Vol: 39, issue: 4, page: 561-77.

The invention claimed is:

1. A diagnostic composition comprising a combination of:
   (a) a polypeptide which comprises an amino acid sequence selected from:
      i) SEQ ID NO: 51 or a fragment hereof having a length of at least 9 amino acids, or
      ii) an amino acid sequence having at least 90% sequence identity to a fragment in i); and
   (b) at least one polypeptide comprising an amino acid sequence selected from:
      i) SEQ ID NO: 54 or
      ii) SEQ ID NO: 55, or
      iii) fragments thereof, wherein said fragments have a length of at least 9 amino acids and comprise an epitope.

2. The diagnostic composition according to claim 1 wherein said fragment of SEQ ID NO: 51 is selected from the group consisting of amino acid sequences as set forth in any one of SEQ ID NOs: 8, 9, 10, 11, 12 and 13.

3. A method for diagnosing previous or ongoing infection with a virulent mycobacterium, e.g. by *Mycobacterium tuberculosis, Mycobacterium africanum* or *Mycobacterium bovis*, said method comprising contacting a sample with a diagnostic composition according to claim 1 in order to detect a positive reaction, such as cell proliferation or release of IFN-gamma or other cytokines such as IL-12, TNF-alpha, IL-4, IL-5, IL-10, IL-6, TGF-beta.

4. A method of diagnosing tuberculosis caused by virulent mycobacteria, e.g. by *Mycobacterium tuberculosis, Mycobacterium africanum* or *Mycobacterium bovis*, in an animal, including a human being, comprising intradermally injecting, in the animal, or applying on the animal's skin a diagnostic composition according to claim 1, a positive skin response at the location of injection or application being indicative of the animal having tuberculosis, and a negative skin response at the location of injection or application being indicative of the animal not having tuberculosis.

* * * * *

SEQUENCE LISTING

```
<160> NUMBER OF SEQ ID NOS: 55

<210> SEQ ID NO 1
<211> LENGTH: 18
<212> TYPE: PRT
<213> ORGANISM: Mycobacterium tuberculosis

<400> SEQUENCE: 1

Met Thr His Lys Arg Thr Lys Arg Gln Pro Ala Ile Ala Ala Gly Leu
1               5                   10                  15

Asn Ala

<210> SEQ ID NO 2
<211> LENGTH: 18
<212> TYPE: PRT
<213> ORGANISM: Mycobacterium tuberculosis

<400> SEQUENCE: 2

Ala Ile Ala Ala Gly Leu Asn Ala Pro Arg Arg Asn Arg Val Gly Arg
1               5                   10                  15

Gln His

<210> SEQ ID NO 3
<211> LENGTH: 18
<212> TYPE: PRT
<213> ORGANISM: Mycobacterium tuberculosis

<400> SEQUENCE: 3

Arg Asn Arg Val Gly Arg Gln His Gly Trp Pro Ala Asp Val Pro Ser
1               5                   10                  15
```

Ala Glu

<210> SEQ ID NO 4
<211> LENGTH: 18
<212> TYPE: PRT
<213> ORGANISM: Mycobacterium tuberculosis

<400> SEQUENCE: 4

Thr Ser His Glu Ile Asp Asp Asp Thr Ala Glu Leu Ala Leu Leu Ser
1               5                   10                  15

Met His

<210> SEQ ID NO 5
<211> LENGTH: 18
<212> TYPE: PRT
<213> ORGANISM: Mycobacterium tuberculosis

<400> SEQUENCE: 5

Glu Leu Ala Leu Leu Ser Met His Leu Asp Asp Glu Gln Arg Arg Leu
1               5                   10                  15

Glu Ala

<210> SEQ ID NO 6
<211> LENGTH: 18
<212> TYPE: PRT
<213> ORGANISM: Mycobacterium tuberculosis

<400> SEQUENCE: 6

Asp Glu Gln Arg Arg Leu Glu Ala Gly Met Lys Leu Gly Trp His Pro
1               5                   10                  15

Tyr His

<210> SEQ ID NO 7
<211> LENGTH: 18
<212> TYPE: PRT
<213> ORGANISM: Mycobacterium tuberculosis

<400> SEQUENCE: 7

Met Lys Leu Gly Trp His Pro Tyr His Phe Pro Asp Glu Pro Asp Ser
1               5                   10                  15

Lys Gln

<210> SEQ ID NO 8
<211> LENGTH: 18
<212> TYPE: PRT
<213> ORGANISM: Mycobacterium tuberculosis

<400> SEQUENCE: 8

Met Ser Gly His Ala Leu Ala Ala Arg Thr Leu Leu Ala Ala Ala Asp
1               5                   10                  15

Glu Leu

<210> SEQ ID NO 9
<211> LENGTH: 18
<212> TYPE: PRT
<213> ORGANISM: Mycobacterium tuberculosis

<400> SEQUENCE: 9

Ala Ala Asp Glu Leu Val Gly Gly Pro Pro Val Glu Ala Ser Ala Ala
1               5                   10                  15

-continued

Ala Leu

<210> SEQ ID NO 10
<211> LENGTH: 18
<212> TYPE: PRT
<213> ORGANISM: Mycobacterium tuberculosis

<400> SEQUENCE: 10

Ala Ser Ala Ala Ala Leu Ala Gly Asp Ala Ala Gly Ala Trp Arg Thr
1               5                   10                  15

Ala Ala

<210> SEQ ID NO 11
<211> LENGTH: 18
<212> TYPE: PRT
<213> ORGANISM: Mycobacterium tuberculosis

<400> SEQUENCE: 11

Ala Trp Arg Thr Ala Ala Val Glu Leu Ala Arg Ala Leu Val Arg Ala
1               5                   10                  15

Val Ala

<210> SEQ ID NO 12
<211> LENGTH: 18
<212> TYPE: PRT
<213> ORGANISM: Mycobacterium tuberculosis

<400> SEQUENCE: 12

Leu Val Arg Ala Val Ala Glu Ser His Gly Val Ala Ala Val Leu Phe
1               5                   10                  15

Ala Ala

<210> SEQ ID NO 13
<211> LENGTH: 18
<212> TYPE: PRT
<213> ORGANISM: Mycobacterium tuberculosis

<400> SEQUENCE: 13

Val Leu Phe Ala Ala Thr Ala Ala Ala Ala Val Asp Arg Gly Asp
1               5                   10                  15

Pro Pro

<210> SEQ ID NO 14
<211> LENGTH: 18
<212> TYPE: PRT
<213> ORGANISM: Mycobacterium tuberculosis

<400> SEQUENCE: 14

Met Leu Trp His Ala Met Pro Pro Glu Leu Asn Thr Ala Arg Leu Met
1               5                   10                  15

Ala Gly

<210> SEQ ID NO 15
<211> LENGTH: 18
<212> TYPE: PRT
<213> ORGANISM: Mycobacterium tuberculosis

<400> SEQUENCE: 15

Ala Arg Leu Met Ala Gly Ala Gly Pro Ala Pro Met Leu Ala Ala Ala
1               5                   10                  15

Ala Gly

```
<210> SEQ ID NO 16
<211> LENGTH: 18
<212> TYPE: PRT
<213> ORGANISM: Mycobacterium tuberculosis

<400> SEQUENCE: 16

Pro Met Leu Ala Ala Ala Ala Gly Trp Gln Thr Leu Ser Ala Ala Leu
1               5                   10                  15

Asp Ala

<210> SEQ ID NO 17
<211> LENGTH: 18
<212> TYPE: PRT
<213> ORGANISM: Mycobacterium tuberculosis

<400> SEQUENCE: 17

Thr Leu Ser Ala Ala Leu Asp Ala Gln Ala Val Glu Leu Thr Ala Arg
1               5                   10                  15

Leu Asn

<210> SEQ ID NO 18
<211> LENGTH: 18
<212> TYPE: PRT
<213> ORGANISM: Mycobacterium tuberculosis

<400> SEQUENCE: 18

Val Glu Leu Thr Ala Arg Leu Asn Ser Leu Gly Glu Ala Trp Thr Gly
1               5                   10                  15

Gly Gly

<210> SEQ ID NO 19
<211> LENGTH: 18
<212> TYPE: PRT
<213> ORGANISM: Mycobacterium tuberculosis

<400> SEQUENCE: 19

Gly Glu Ala Trp Thr Gly Gly Gly Ser Asp Lys Ala Leu Ala Ala Ala
1               5                   10                  15

Thr Pro

<210> SEQ ID NO 20
<211> LENGTH: 18
<212> TYPE: PRT
<213> ORGANISM: Mycobacterium tuberculosis

<400> SEQUENCE: 20

Lys Thr Arg Ala Met Gln Ala Thr Ala Gln Ala Ala Tyr Thr Gln
1               5                   10                  15

Ala Met

<210> SEQ ID NO 21
<211> LENGTH: 18
<212> TYPE: PRT
<213> ORGANISM: Mycobacterium tuberculosis

<400> SEQUENCE: 21

Ala Ala Tyr Thr Gln Ala Met Ala Thr Thr Pro Ser Leu Pro Glu Ile
1               5                   10                  15

Ala Ala
```

```
<210> SEQ ID NO 22
<211> LENGTH: 18
<212> TYPE: PRT
<213> ORGANISM: Mycobacterium tuberculosis

<400> SEQUENCE: 22

Leu Pro Glu Ile Ala Ala Asn His Ile Thr Gln Ala Val Leu Thr Ala
1               5                   10                  15

Thr Asn

<210> SEQ ID NO 23
<211> LENGTH: 18
<212> TYPE: PRT
<213> ORGANISM: Mycobacterium tuberculosis

<400> SEQUENCE: 23

Asn Thr Ile Pro Ile Ala Leu Thr Glu Met Asp Tyr Phe Ile Arg Met
1               5                   10                  15

Trp Asn

<210> SEQ ID NO 24
<211> LENGTH: 18
<212> TYPE: PRT
<213> ORGANISM: Mycobacterium tuberculosis

<400> SEQUENCE: 24

Ala Ala Leu Ala Met Glu Val Tyr Gln Ala Glu Thr Ala Val Asn Thr
1               5                   10                  15

Leu Phe

<210> SEQ ID NO 25
<211> LENGTH: 18
<212> TYPE: PRT
<213> ORGANISM: Mycobacterium tuberculosis

<400> SEQUENCE: 25

Glu Thr Ala Val Asn Thr Leu Phe Glu Lys Leu Glu Pro Met Ala Ser
1               5                   10                  15

Ile Leu

<210> SEQ ID NO 26
<211> LENGTH: 18
<212> TYPE: PRT
<213> ORGANISM: Mycobacterium tuberculosis

<400> SEQUENCE: 26

Leu Glu Pro Met Ala Ser Ile Leu Asp Pro Gly Ala Ser Gln Ser Thr
1               5                   10                  15

Thr Asn

<210> SEQ ID NO 27
<211> LENGTH: 18
<212> TYPE: PRT
<213> ORGANISM: Mycobacterium tuberculosis

<400> SEQUENCE: 27

Gly Ala Ser Gln Ser Thr Thr Asn Pro Ile Phe Gly Met Pro Ser Pro
1               5                   10                  15

Gly Ser
```

```
<210> SEQ ID NO 28
<211> LENGTH: 18
<212> TYPE: PRT
<213> ORGANISM: Mycobacterium tuberculosis

<400> SEQUENCE: 28

Pro Val Gly Gln Leu Pro Pro Ala Ala Thr Gln Thr Leu Gly Gln Leu
1               5                   10                  15
Gly Glu

<210> SEQ ID NO 29
<211> LENGTH: 18
<212> TYPE: PRT
<213> ORGANISM: Mycobacterium tuberculosis

<400> SEQUENCE: 29

Gly Pro Met Gln Gln Leu Thr Gln Pro Leu Gln Gln Val Thr Ser Leu
1               5                   10                  15
Phe Ser

<210> SEQ ID NO 30
<211> LENGTH: 18
<212> TYPE: PRT
<213> ORGANISM: Mycobacterium tuberculosis

<400> SEQUENCE: 30

Gly Gly Thr Gly Gly Gly Asn Pro Ala Asp Glu Glu Ala Ala Gln Met
1               5                   10                  15
Gly Leu

<210> SEQ ID NO 31
<211> LENGTH: 18
<212> TYPE: PRT
<213> ORGANISM: Mycobacterium tuberculosis

<400> SEQUENCE: 31

Thr Ser Pro Leu Ser Asn His Pro Leu Ala Gly Gly Ser Gly Pro Ser
1               5                   10                  15
Ala Gly

<210> SEQ ID NO 32
<211> LENGTH: 18
<212> TYPE: PRT
<213> ORGANISM: Mycobacterium tuberculosis

<400> SEQUENCE: 32

Gly Gly Ser Leu Thr Arg Thr Pro Leu Met Ser Gln Leu Ile Glu Lys
1               5                   10                  15
Pro Val

<210> SEQ ID NO 33
<211> LENGTH: 18
<212> TYPE: PRT
<213> ORGANISM: Mycobacterium tuberculosis

<400> SEQUENCE: 33

Ala Thr Gly Gly Ala Ala Pro Val Gly Ala Gly Ala Met Gly Gln Gly
1               5                   10                  15
Ala Gln

<210> SEQ ID NO 34
```

-continued

```
<211> LENGTH: 18
<212> TYPE: PRT
<213> ORGANISM: Mycobacterium tuberculosis

<400> SEQUENCE: 34

Ala Met Gly Gln Gly Ala Gln Ser Gly Gly Ser Thr Arg Pro Gly Leu
1               5                   10                  15

Val Ala

<210> SEQ ID NO 35
<211> LENGTH: 18
<212> TYPE: PRT
<213> ORGANISM: Mycobacterium tuberculosis

<400> SEQUENCE: 35

Ala Gln Glu Arg Glu Glu Asp Asp Glu Asp Asp Trp Asp Glu Glu Asp
1               5                   10                  15

Asp Trp

<210> SEQ ID NO 36
<211> LENGTH: 20
<212> TYPE: PRT
<213> ORGANISM: Mycobacterium tuberculosis

<400> SEQUENCE: 36

Ala Glu Pro Leu Ala Val Asp Pro Thr Gly Leu Ser Ala Ala Ala Ala
1               5                   10                  15

Lys Leu Ala Gly
            20

<210> SEQ ID NO 37
<211> LENGTH: 20
<212> TYPE: PRT
<213> ORGANISM: Mycobacterium tuberculosis

<400> SEQUENCE: 37

Gln Pro Pro Ala Pro Ile Ala Val Ser Gly Thr Asp Ser Val Val Ala
1               5                   10                  15

Ala Ile Asn Glu
            20

<210> SEQ ID NO 38
<211> LENGTH: 20
<212> TYPE: PRT
<213> ORGANISM: Mycobacterium tuberculosis

<400> SEQUENCE: 38

Ser Val Val Ala Ala Ile Asn Glu Thr Met Pro Ser Ile Glu Ser Leu
1               5                   10                  15

Val Ser Asp Gly
            20

<210> SEQ ID NO 39
<211> LENGTH: 20
<212> TYPE: PRT
<213> ORGANISM: Mycobacterium tuberculosis

<400> SEQUENCE: 39

Ile Glu Ser Leu Val Ser Asp Gly Leu Pro Gly Val Lys Ala Ala Leu
1               5                   10                  15

Thr Arg Thr Ala
            20
```

<210> SEQ ID NO 40
<211> LENGTH: 20
<212> TYPE: PRT
<213> ORGANISM: Mycobacterium tuberculosis

<400> SEQUENCE: 40

Lys Ala Ala Leu Thr Arg Thr Ala Ser Asn Met Asn Ala Ala Ala Asp
1               5                   10                  15

Val Tyr Ala Lys
            20

<210> SEQ ID NO 41
<211> LENGTH: 20
<212> TYPE: PRT
<213> ORGANISM: Mycobacterium tuberculosis

<400> SEQUENCE: 41

Ala Ala Ala Asp Val Tyr Ala Lys Thr Asp Gln Ser Leu Gly Thr Ser
1               5                   10                  15

Leu Ser Gln Tyr
            20

<210> SEQ ID NO 42
<211> LENGTH: 20
<212> TYPE: PRT
<213> ORGANISM: Mycobacterium tuberculosis

<400> SEQUENCE: 42

Leu Gly Thr Ser Leu Ser Gln Tyr Ala Phe Gly Ser Ser Gly Glu Gly
1               5                   10                  15

Leu Ala Gly Val
            20

<210> SEQ ID NO 43
<211> LENGTH: 20
<212> TYPE: PRT
<213> ORGANISM: Mycobacterium tuberculosis

<400> SEQUENCE: 43

Ser Gly Glu Gly Leu Ala Gly Val Ala Ser Val Gly Gly Gln Pro Ser
1               5                   10                  15

Gln Ala Thr Gln
            20

<210> SEQ ID NO 44
<211> LENGTH: 20
<212> TYPE: PRT
<213> ORGANISM: Mycobacterium tuberculosis

<400> SEQUENCE: 44

Pro Val Ser Gln Val Thr Thr Gln Leu Gly Glu Thr Ala Ala Glu Leu
1               5                   10                  15

Ala Pro Arg Val
            20

<210> SEQ ID NO 45
<211> LENGTH: 20
<212> TYPE: PRT
<213> ORGANISM: Mycobacterium tuberculosis

<400> SEQUENCE: 45

-continued

```
Ala Ala Glu Leu Ala Pro Arg Val Val Ala Thr Val Pro Gln Leu Val
1               5                   10                  15

Gln Leu Ala Pro
            20

<210> SEQ ID NO 46
<211> LENGTH: 20
<212> TYPE: PRT
<213> ORGANISM: Mycobacterium tuberculosis

<400> SEQUENCE: 46

Pro Gln Leu Val Gln Leu Ala Pro His Ala Val Gln Met Ser Gln Asn
1               5                   10                  15

Ala Ser Pro Ile
            20

<210> SEQ ID NO 47
<211> LENGTH: 20
<212> TYPE: PRT
<213> ORGANISM: Mycobacterium tuberculosis

<400> SEQUENCE: 47

Met Ser Gln Asn Ala Ser Pro Ile Ala Gln Thr Ile Ser Gln Thr Ala
1               5                   10                  15

Gln Gln Ala Ala
            20

<210> SEQ ID NO 48
<211> LENGTH: 20
<212> TYPE: PRT
<213> ORGANISM: Mycobacterium tuberculosis

<400> SEQUENCE: 48

Ser Gln Thr Ala Gln Gln Ala Ala Gln Ser Ala Gln Gly Gly Ser Gly
1               5                   10                  15

Pro Met Pro Ala
            20

<210> SEQ ID NO 49
<211> LENGTH: 20
<212> TYPE: PRT
<213> ORGANISM: Mycobacterium tuberculosis

<400> SEQUENCE: 49

Ala Glu Lys Pro Ala Thr Glu Gln Ala Glu Pro Val His Glu Val Thr
1               5                   10                  15

Asn Asp Asp Gln
            20

<210> SEQ ID NO 50
<211> LENGTH: 20
<212> TYPE: PRT
<213> ORGANISM: Mycobacterium tuberculosis

<400> SEQUENCE: 50

Ser Pro Leu Ala Ala Pro Val Asp Pro Ser Thr Pro Ala Pro Ser Thr
1               5                   10                  15

Thr Thr Thr Leu
            20

<210> SEQ ID NO 51
<211> LENGTH: 81
```

-continued

<212> TYPE: PRT
<213> ORGANISM: M Tuberculosis

<400> SEQUENCE: 51

Met Ser Gly His Ala Leu Ala Ala Arg Thr Leu Leu Ala Ala Ala Asp
1               5                   10                  15

Glu Leu Val Gly Gly Pro Pro Val Glu Ala Ser Ala Ala Ala Leu Ala
            20                  25                  30

Gly Asp Ala Ala Gly Ala Trp Arg Thr Ala Ala Val Glu Leu Ala Arg
        35                  40                  45

Ala Leu Val Arg Ala Val Ala Glu Ser His Gly Val Ala Ala Val Leu
    50                  55                  60

Phe Ala Ala Thr Ala Ala Ala Ala Ala Ala Val Asp Arg Gly Asp Pro
65                  70                  75                  80

Pro

<210> SEQ ID NO 52
<211> LENGTH: 107
<212> TYPE: PRT
<213> ORGANISM: Mycobacterium Tuberculosis

<400> SEQUENCE: 52

Met Thr His Lys Arg Thr Lys Arg Gln Pro Ala Ile Ala Ala Gly Leu
1               5                   10                  15

Asn Ala Pro Arg Arg Asn Arg Val Gly Arg Gln His Gly Trp Pro Ala
            20                  25                  30

Asp Val Pro Ser Ala Glu Gln Arg Arg Ala Gln Arg Gln Arg Asp Leu
        35                  40                  45

Glu Ala Ile Arg Arg Ala Tyr Ala Glu Met Val Ala Thr Ser His Glu
    50                  55                  60

Ile Asp Asp Asp Thr Ala Glu Leu Ala Leu Leu Ser Met His Leu Asp
65                  70                  75                  80

Asp Glu Gln Arg Arg Leu Glu Ala Gly Met Lys Leu Gly Trp His Pro
                85                  90                  95

Tyr His Phe Pro Asp Glu Pro Asp Ser Lys Gln
            100                 105

<210> SEQ ID NO 53
<211> LENGTH: 280
<212> TYPE: PRT
<213> ORGANISM: Mycobacterium tuberculosis

<400> SEQUENCE: 53

Met Ala Glu Pro Leu Ala Val Asp Pro Thr Gly Leu Ser Ala Ala Ala
1               5                   10                  15

Ala Lys Leu Ala Gly Leu Val Phe Pro Gln Pro Pro Ala Pro Ile Ala
            20                  25                  30

Val Ser Gly Thr Asp Ser Val Val Ala Ala Ile Asn Glu Thr Met Pro
        35                  40                  45

Ser Ile Glu Ser Leu Val Ser Asp Gly Leu Pro Gly Val Lys Ala Ala
    50                  55                  60

Leu Thr Arg Thr Ala Ser Asn Met Asn Ala Ala Ala Asp Val Tyr Ala
65                  70                  75                  80

Lys Thr Asp Gln Ser Leu Gly Thr Ser Leu Ser Gln Tyr Ala Phe Gly
                85                  90                  95

Ser Ser Gly Glu Gly Leu Ala Gly Val Ala Ser Val Gly Gly Gln Pro
            100                 105                 110

```
Ser Gln Ala Thr Gln Leu Leu Ser Thr Pro Val Ser Gln Val Thr Thr
        115                 120                 125

Gln Leu Gly Glu Thr Ala Ala Glu Leu Ala Pro Arg Val Val Ala Thr
        130                 135                 140

Val Pro Gln Leu Val Gln Leu Ala Pro His Ala Val Gln Met Ser Gln
145                 150                 155                 160

Asn Ala Ser Pro Ile Ala Gln Thr Ile Ser Gln Thr Ala Gln Gln Ala
                165                 170                 175

Ala Gln Ser Ala Gln Gly Gly Ser Gly Pro Met Pro Ala Gln Leu Ala
        180                 185                 190

Ser Ala Glu Lys Pro Ala Thr Glu Gln Ala Glu Pro Val His Glu Val
        195                 200                 205

Thr Asn Asp Asp Gln Gly Asp Gln Gly Asp Val Gln Pro Ala Glu Val
        210                 215                 220

Val Ala Ala Arg Asp Glu Gly Ala Gly Ala Ser Pro Gly Gln Gln
225                 230                 235                 240

Pro Gly Gly Gly Val Pro Ala Gln Ala Met Asp Thr Gly Ala Gly Ala
                245                 250                 255

Arg Pro Ala Ala Ser Pro Leu Ala Ala Pro Val Asp Pro Ser Thr Pro
        260                 265                 270

Ala Pro Ser Thr Thr Thr Thr Leu
        275                 280

<210> SEQ ID NO 54
<211> LENGTH: 95
<212> TYPE: PRT
<213> ORGANISM: Mycobacterium Tuberculosis

<400> SEQUENCE: 54

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 55
<211> LENGTH: 100
<212> TYPE: PRT
<213> ORGANISM: Mycobacterium Tuberculosis

<400> SEQUENCE: 55

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60
```

```
Gln Lys Gln Glu Leu Asp Glu Ile Ser Thr Asn Ile Arg Gln Ala Gly
 65                  70                  75                  80

Val Gln Tyr Ser Arg Ala Asp Glu Glu Gln Gln Gln Ala Leu Ser Ser
                 85                  90                  95

Gln Met Gly Phe
            100
```